United States Patent
Hazama

(10) Patent No.: US 10,893,872 B2
(45) Date of Patent: *Jan. 19, 2021

(54) HEMOSTATIC DEVICE

(71) Applicant: TERUMO KABUSHIKI KAISHA, Tokyo (JP)

(72) Inventor: Kenichi Hazama, Bear, DE (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 110 days.

This patent is subject to a terminal disclaimer.

(21) Appl. No.: 16/138,032

(22) Filed: Sep. 21, 2018

(65) Prior Publication Data

US 2019/0021742 A1 Jan. 24, 2019

Related U.S. Application Data

(63) Continuation of application No. PCT/JP2017/011485, filed on Mar. 22, 2017.

(30) Foreign Application Priority Data

Mar. 23, 2016 (JP) ................................ 2016-058217

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1322* (2013.01); *A61B 90/08* (2016.02);
(Continued)

(58) Field of Classification Search
CPC combination set(s) only.
See application file for complete search history.

(56) References Cited

U.S. PATENT DOCUMENTS 5,703,804 A * 12/1997 Takata ................... G11C 5/143
365/145
10,575,859 B2 * 3/2020 Hazama ............... A61B 17/135
(Continued)

FOREIGN PATENT DOCUMENTS

JP   H6-31816 A   2/1994
JP   H0621608 U   3/1994
(Continued)

OTHER PUBLICATIONS

The extended European Search Report dated Oct. 16, 2019, by the European Patent Office in corresponding European Patent Application No. 17770282.6-1122. (8 pages).
(Continued)

*Primary Examiner* — Jocelin C Tanner
(74) *Attorney, Agent, or Firm* — Buchanan Ingersoll & Rooney PC

(57) ABSTRACT

A hemostatic device includes a band configured to be wrapped around a wrist, and to be secured in a state where the band is wrapped around the wrist, and an inflatable portion that interlocks with the band and that is inflated by injecting gas. The inflatable portion has a first region formed of a thermoplastic material and a second region formed of a thermosetting elastomer whose gas permeability is higher than that of the thermoplastic material. The band has an interlock region which is formed of the thermoplastic material, and with which the inflatable portion interlocks. The first region of the inflatable portion is welded to the interlock region of the band. The compressing force of the inflatable portion can be reduced over time to inhibit vascular occlusion.

20 Claims, 12 Drawing Sheets

(51) Int. Cl.
  *A61B 90/00* (2016.01)
  *A61B 17/00* (2006.01)
  *A61B 17/12* (2006.01)
(52) U.S. Cl.
  CPC .............. *A61B 2017/00477* (2013.01); *A61B 2017/00526* (2013.01); *A61B 2017/00557* (2013.01); *A61B 2017/00831* (2013.01); *A61B 2017/00862* (2013.01); *A61B 2017/00907* (2013.01); *A61B 2017/00955* (2013.01); *A61B 2017/12004* (2013.01); *A61B 2090/0811* (2016.02)

(56) References Cited

U.S. PATENT DOCUMENTS

| | | | |
|---|---|---|---|
| 2004/0098035 A1* | 5/2004 | Wada ................... | A61B 17/135 606/201 |
| 2011/0077564 A1 | 3/2011 | Ganapathy et al. | |
| 2015/0025478 A1* | 1/2015 | Hibdon ................ | A61M 39/04 604/288.01 |

FOREIGN PATENT DOCUMENTS

| | | |
|---|---|---|
| JP | 2004201829 A | 7/2004 |
| JP | 2005318998 A | 11/2005 |
| JP | 2007021112 A | 2/2007 |
| JP | 2014200308 A | 10/2014 |

OTHER PUBLICATIONS

An English Translation of the International Search Report (Form PCT/ISA/210) and the Written Opinion of the International Searching Authority (Form PCT/ISA/237) dated Jun. 27, 2017 by the Japanese Patent Office in corresponding International Application No. PCT/JP2017/011485 (8 pages).
International Search Report (PCT/ISA/210) dated Jun. 27, 2017, by the Japan Patent Office as the International Searching Authority for International Application No. PCT/JP2017/011485.
Written Opinion (PCT/ISA/237) dated Jun. 27, 2017, by the Japan Patent Office as the International Searching Authority for International Application No. PCT/JP2017/011485.

* cited by examiner

HEMOSTATIC DEVICE

CROSS-REFERENCES TO RELATED APPLICATIONS

This application is a continuation of International Application No. PCT/JP2017/011485 filed on Mar. 22, 2017 which claims priority to Japanese Application No. 2016-058217 filed on Mar. 23, 2016, the entire content of both of which is incorporated herein by reference.

TECHNICAL FIELD

The present invention generally relates to a hemostatic device used for performing hemostasis by compressing a punctured site.

BACKGROUND DISCUSSION

In recent years, percutaneous treatment and examination have been performed in which a blood vessel in the arms or legs is punctured and an introducer sheath is introduced into a puncture site so as to deliver a medical device such as a catheter to a lesion area via a lumen of the introducer sheath. In a case where this treatment and examination are performed, an operator needs to perform hemostasis at the puncture site after the introducer sheath is removed from the puncture site. In order to perform this hemostasis, a hemostatic device is known which includes a band for being wrapped around a limb such as arms and legs, means for securing the band in a state where the band is wrapped around the limb, and an inflatable portion that interlocks with the band, and that is inflated by injecting a fluid so as to compress the puncture site.

According to this hemostatic device, if the inflated inflatable portion continues to strongly compress the puncture site and a blood vessel or a nerve around the puncture site for a long time, there is a possibility that numbness or pain may be caused or the blood vessel may be occluded. In order to prevent the vascular occlusion, a physician or a nurse generally inflates the inflatable portion, and thereafter, he or she periodically connects a dedicated instrument such as a syringe to the hemostatic device, discharges fluid inside the inflatable portion, and performs a decompressing operation for reducing internal pressure of the inflatable portion, thereby reducing a compressing force acting on the puncture site over time.

In contrast, according to the hemostatic device disclosed in Japanese Patent Application Publication No. 2004-201829, the inflatable portion is configured to include a material stretching over time. Therefore, after the inflatable portion is inflated by injecting the fluid into the inflatable portion, the inflatable portion is gradually inflated and deformed by pressure applied from the fluid inside the inflatable portion. Whereas the amount of the fluid inside the inflatable portion is constant, a volume in an internal space of the inflatable portion gradually increases. Accordingly, internal pressure of the inflatable portion can be reduced over time. In this manner, the compressing force acting on the puncture site can be reduced with the lapse of time.

SUMMARY

According to the hemostatic device disclosed in Japanese Patent Application Publication No. 2004-201829, the physician or the nurse can save time and effort when performing the decompressing operation. However, if the inflatable portion is configured to include the material that stretches over time, the inflatable portion is progressively inflated and deformed over time. As a result, the thickness of the inflatable portion becomes thinner. From a viewpoint of satisfactorily maintaining the strength of the inflatable portion, it is preferable that the thickness of the inflatable portion is preferably maintained to some extent.

For example, if the inflatable portion is configured to include a material having high gas permeability, after gas is injected into the inflatable portion so as to inflate the inflatable portion, the gas contained inside the inflatable portion is discharged outward over time. Accordingly, without decreasing the thickness of the inflatable portion, the internal pressure of the inflatable portion can be reduced over time. In this case, in order to maintain the thickness of the inflatable portion to some extent and allow the gas to be discharged to such an extent that the vascular occlusion can be prevented, it is preferable that the inflatable portion is configured to include a thermosetting elastomer having particularly high gas permeability. However, if the inflatable portion is formed of the thermosetting elastomer, a band and the inflatable portion cannot be interlocked by means of welding due to the influence of material properties.

The hemostatic device disclosed here can satisfactorily maintain the strength of an inflatable portion, which does not need to be operated by a physician or a nurse, whose compressing force acting on a site where bleeding is to be stopped can be reduced over time to such an extent that vascular occlusion can be prevented, and in which the inflatable portion and a band are interlocked with each other by means of welding.

According to one aspect, a hemostatic device comprises a band for being wrapped around a site where bleeding is to be stopped on a limb, means for securing the band in a state where the band is wrapped around the limb, and an inflatable portion that interlocks with the band, that is inflated by injecting gas, and that applies a compressive force at the site where bleeding is to be stopped. The inflatable portion includes a first region formed of a thermoplastic material and a second region formed of a thermosetting elastomer whose gas permeability is higher than that of the thermoplastic material. The band includes an interlock region which is formed of the thermoplastic material, and with which the inflatable portion interlocks, and the first region of the inflatable portion is welded to the interlock region of the band.

According to the hemostatic device configured as described above, after the inflatable portion is inflated, the gas contained inside the inflatable portion is discharged outward of the inflatable portion via the second region formed of the thermosetting elastomer with the lapse of time to such an extent that vascular occlusion can be prevented. In this case, the second region formed of the thermosetting elastomer has relatively high gas permeability. Accordingly, it is not necessary to excessively decrease a thickness of the inflatable portion in order to increase a gas permeable amount. Therefore, the hemostatic device can satisfactorily maintain strength of the inflatable portion, and does not need to be operated by a physician or a nurse, in which a compressing force acting on a site where bleeding is to be stopped can be reduced with the lapse of time to such an extent that vascular occlusion can be prevented. Furthermore, the first region formed of the thermoplastic material is disposed in the inflatable portion, and the interlock region formed of the thermoplastic material is disposed in the band. Therefore, the first region and the interlock region are welded to each other, so that it is possible to provide the hemostatic device in which the inflatable portion and the band are interlocked with each other.

According to another aspect, a hemostatic device comprises a belt configured to be wrapped around a limb of a patient adjacent a site where bleeding is to be stopped, a plate more rigid than the belt, the plate being held by the belt, means for securing the belt in a wrapped state around the patient's limb, and an inflatable portion that inflates upon injecting gas into an interior of the inflatable portion to apply a compressive force to the site at which bleeding is to be stopped. The inflatable portion includes a first region and a second region, with the first region positioned along an outermost periphery of the inflatable portion and comprising a first plastic material, and the second region positioned inwardly of the first region and expanding outwardly when the gas is introduced into the inflatable portion to inflate the inflatable portion. The second region is comprised of a second plastic material different form the first plastic material. The second region possesses gas permeability allowing the gas introduced into the balloon to inflate the inflatable portion to permeate through the second region over time to reduce pressure in the interior of the inflatable portion. A portion of the first region of the inflatable portion is welded to a part of the belt to fix the inflatable portion relative to the belt.

In accordance with another aspect, a hemostatic device comprises a belt configured to be wrapped around a limb of a patient adjacent a site where bleeding is to be stopped, a plate more rigid than the belt, the plate being held by the belt, means for securing the belt in a wrapped state around the patient's limb, and an inflatable portion that is inflated upon injecting gas into the inflatable portion to apply a compressive force to the site at which bleeding is to be stopped. The inflatable portion is fixed to the belt on a side of the belt that faces the limb of the patient when the belt is in the wrapped state. The inflatable portion comprises a first surface that faces the limb of the patient when the belt is in the wrapped state and a second surface that faces toward the band when the belt is in the wrapped state. The first surface or the second surface is comprised of a first region and a second region, with the first region being positioned outwardly of the second region and being made of a first plastic material, and with the second region being made of a second plastic material different from the first plastic material. The first and second regions each possess a respective gas permeability, and the gas permeability of the second region is greater than the gas permeability of the first region to permit the gas introduced into the balloon to inflate the inflatable portion to permeate through the second region over time to reduce pressure in the inflatable portion.

BRIEF DESCRIPTION OF THE DRAWINGS

FIGS. 3(A), 3(B) and 3(C) are plan views illustrating an inflatable portion of the hemostatic device according to the embodiment, in which FIG. 3(A) is a view illustrating a first sheet configuring the inflatable portion, FIG. 3(B) is a view illustrating a second sheet configuring the inflatable portion, and FIG. 3(C) is a view for describing a welding portion in the inflatable portion.

FIG. 9(A) is a view illustrating a state where the inflatable portion is covered with a sealing member. FIG. 9(B) is a view illustrating a state where the sealing member is detached.

FIGS. 11(A) and 11(B) are views for describing an example and a comparative example, in which FIG. 11(A) is a view illustrating a time-dependent change in an air volume inside the inflatable portion, and FIG. 11(B) is a view illustrating a time-dependent change in internal pressure of the inflatable portion.

DETAILED DESCRIPTION

Figure 1:
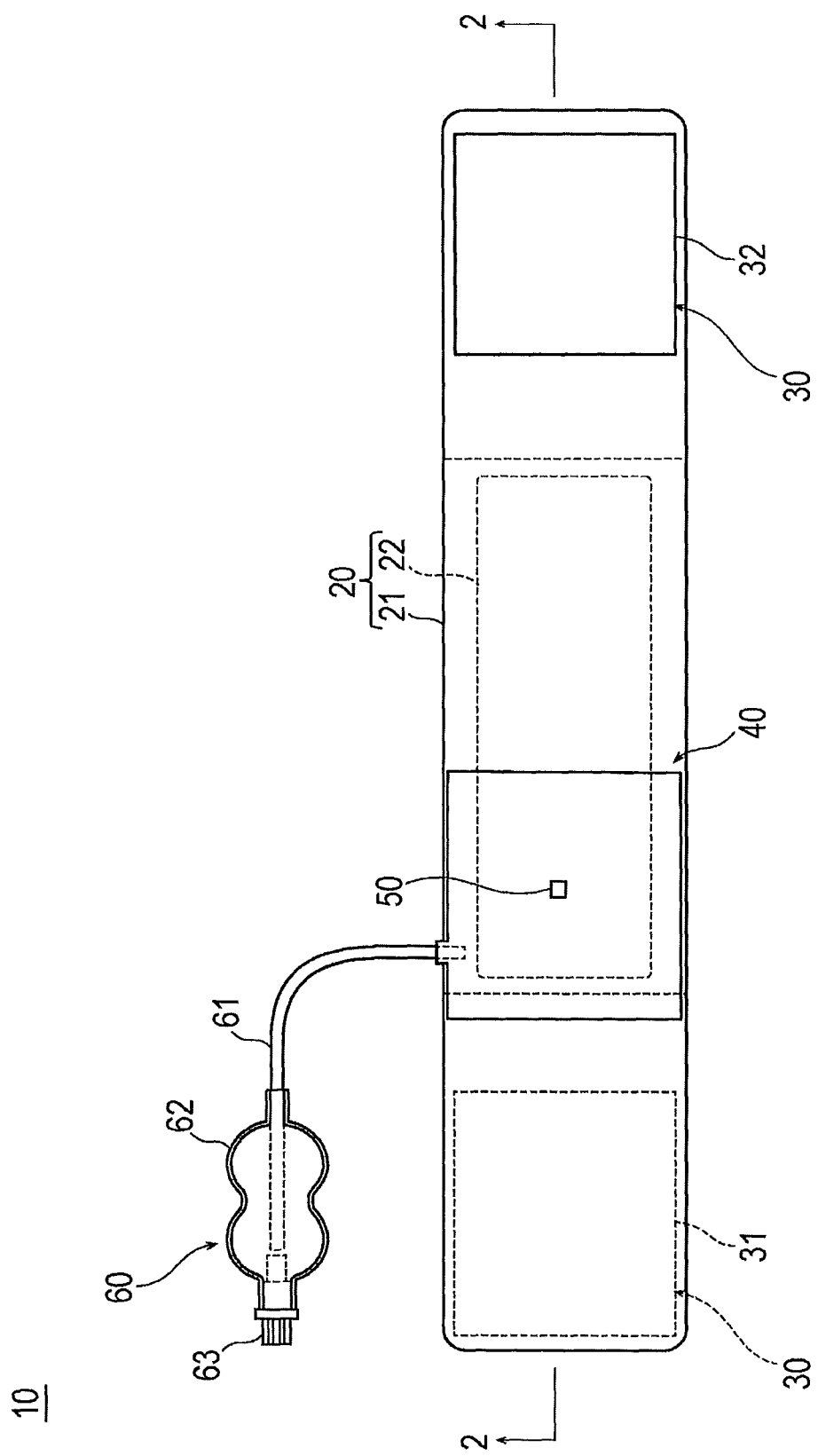
FIG. 1 is a plan view of a hemostatic device according to an embodiment as viewed from an inner surface side.

Set forth below with reference to the accompanying drawings is a detailed description of embodiments of a hemostatic device and operational method representing examples of the inventive hemostatic device and operational method disclosed here. The following description does not limit the technical scope or the meaning of terms described in appended claims. In addition, dimensional proportions in the drawings are exaggerated and different from actual proportions for convenience of description and to facilitate an understanding, in some cases.

Figure 4:
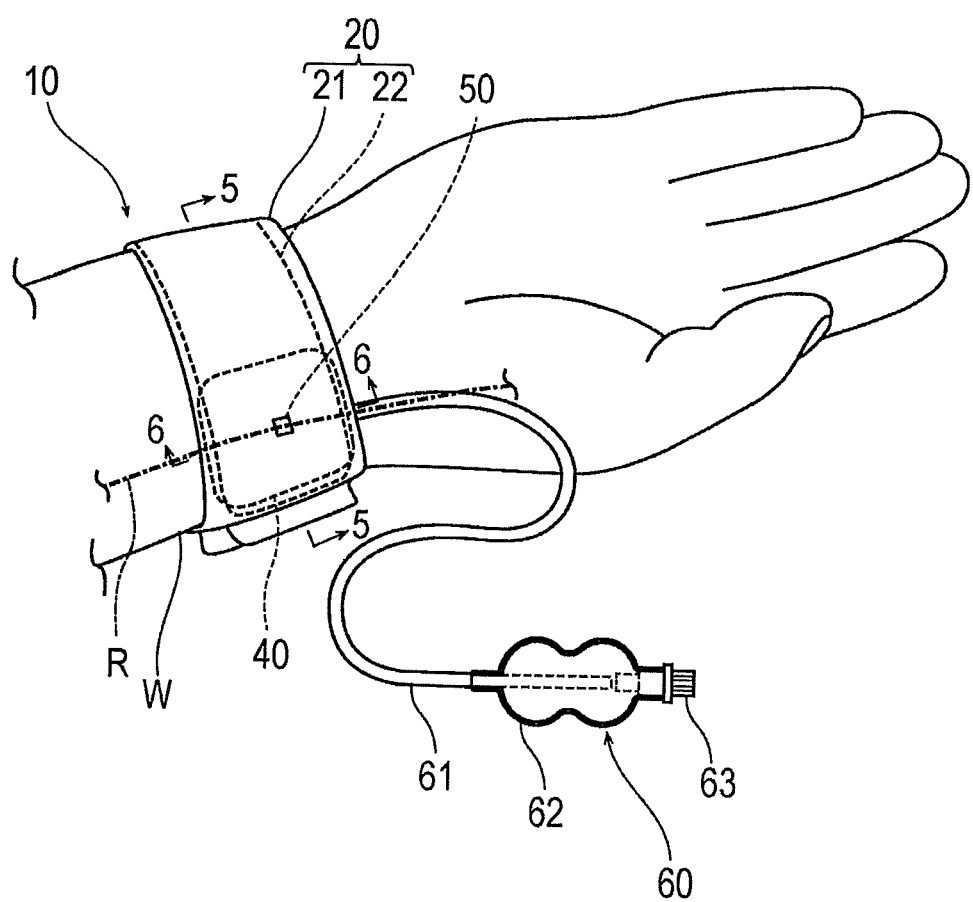
FIG. 4 is a perspective view illustrating a state where the hemostatic device according to the embodiment is worn on a wrist.
Figure 5:
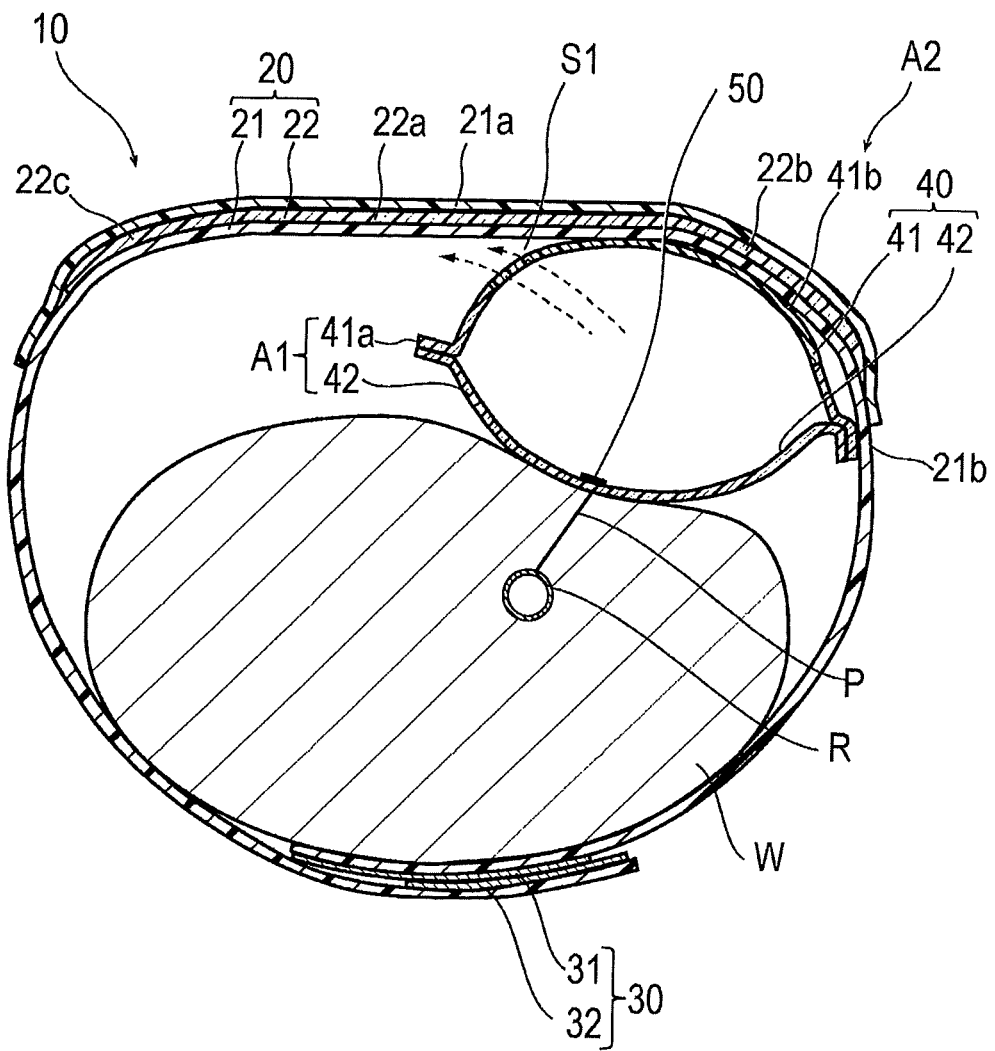
FIG. 5 is a cross-sectional view taken along the section line 5-5 in FIG. 4.

As illustrated in FIGS. 4 and 5, a hemostatic device 10 according to the embodiment is used for performing hemostasis on a puncture site P (corresponding to a "site where bleeding is to be stopped") formed in a radial artery R of a wrist W (corresponding to a "limb") in order to insert a catheter for performing treatment and examination into a blood vessel, after an introducer sheath indwelling the puncture site P is removed.

Figure 2:
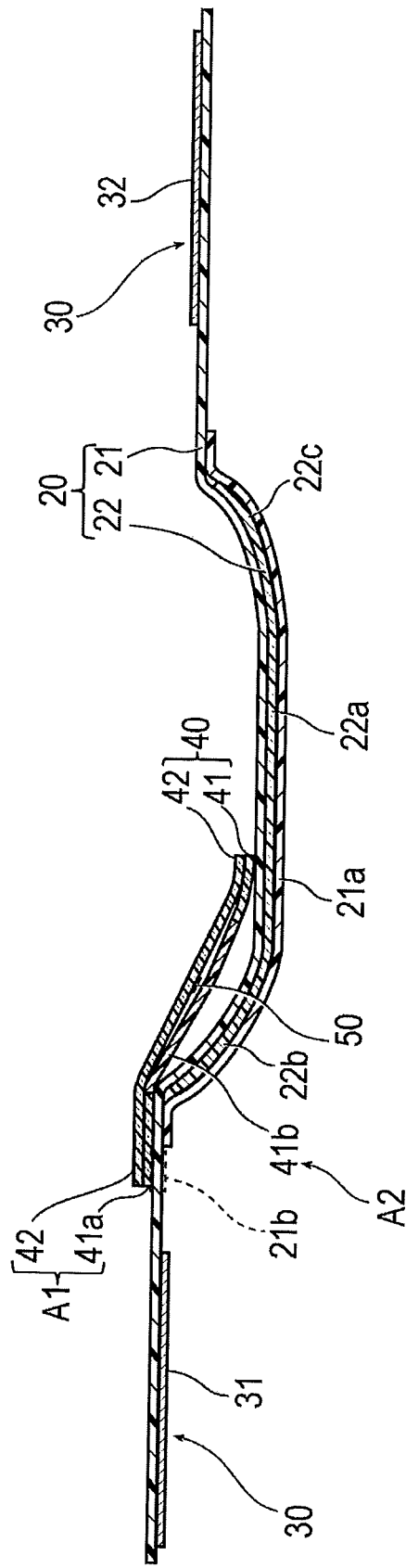
FIG. 2 is a cross-sectional view taken along the section line 2-2 in FIG. 1.

As illustrated in FIGS. 1 and 2, the hemostatic device 10 may include a band 20 for being wrapped around the wrist W, a surface fastener 30 (representing one example of "means for securing") for securing the band 20 in a state where the band 20 is wrapped around the wrist W, an inflatable portion 40 that is inflated by injecting gas into the inflatable portion 40 so as to compress the puncture site P, a marker 50 for aligning the inflatable portion 40 with the puncture site P, and an injection part 60 that can inject gas into the inflatable portion 40.

In the following description, when the band 20 is in a state of being wrapped around the wrist W, a side (wearing surface side) facing a body surface of the wrist W in the band 20 will be referred to as an "inner surface side", and a side opposite the wearing surface side will be referred to as an "outer surface side".

The band 20 includes a belt 21 configured to include a flexible belt-like member, and a support plate 22 which is more rigid than the belt 21.

As illustrated in FIGS. 4 and 5, the belt 21 is wrapped substantially once or with one wrapping around an outer periphery of the wrist W. As illustrated in FIG. 2, a support plate holder 21a for holding the support plate 22 is formed in a central portion of the belt 21. The support plate holder 21a is adapted to have double structures (two layers of material) in such a way that a separate belt-like member is joined to the outer surface side (or the inner surface side) by welding (heat-welding, high frequency welding, or ultrasound welding) or adhesion (adhesion using an adhesive or a solvent), thereby holding the support plate 22 inserted into a gap between the double structures.

A male side (or a female side) 31 of the surface fastener 30 generally called a Magic Tape (registered trademark) is located on the outer surface side of a portion in the vicinity of the left end in FIG. 1 of the belt 21, and a female side (or a male side) 32 of the surface fastener 30 is located on the inner surface side of a portion in the vicinity of the right end in FIG. 1 of the belt 21. As illustrated in FIG. 5, the belt 21 is wrapped around the wrist W, and the male side 31 and the female side 32 are joined to each other. In this manner, the band 20 is worn or held on the wrist W. The means for securing the band 20 is not limited to the surface fastener 30. Examples of other possible structures constituting the means for securing the band 20 in a state where the band 20 is wrapped around the wrist W include a snap, a button, a clip, or a frame member passing through the end portion of the belt 21.

It is preferable that the belt 21 is configured to include a thermoplastic material in order to enable the inflatable portion 40 (to be described later) to be interlocked by welding. The belt 21 may be configured as follows. As long as an interlock region 21b (in the present embodiment, as illustrated in FIG. 2, a region between a region having a first curved portion 22b of the support plate 22 (to be described later) and a region to which the male side 31 of the surface fastener 30 is attached) with which at least the inflatable portion 40 is interlocked are configured to include the thermoplastic material (are comprised of thermoplastic material), a portion other than the interlock region 21b may be formed of a material other than the thermoplastic material.

In addition, the belt 21 is preferably configured to include a material whose elastic modulus is higher than that of a material configuring a second region A2 of the inflatable portion 40 (to be described later). For example, in a case where the second region A2 of the inflatable portion 40 is configured to include silicone rubber, a thermoplastic material can be used for a configuration material of the belt 21. As an example of the thermoplastic material, it is possible to use a thermoplastic resin such as polyvinyl chloride, polyethylene, polypropylene, and polyvinylidene chloride, or various thermoplastic elastomers such as an olefinic thermoplastic elastomer and a styrene thermoplastic elastomer. Since the belt 21 is formed of this material, the belt 21 is relatively less likely to stretch. Without being affected by a wearer's size of the wrist W, it is possible to suitably maintain a state where the inflatable portion 40 is pressed on the wrist W.

In addition, it is preferable that at least a portion overlapping the inflatable portion 40 in the belt 21 is substantially transparent. However, without being limited to transparency, the portion may be translucent or colored transparent. In this manner, the puncture site P is visible from the outer surface side, thereby enabling the marker 50 (to be described later) to rather easily align with the puncture site P.

As illustrated in FIG. 2, the support plate 22 is inserted between the support plate holders 21a, which are double-formed (i.e., double layer of material) in the belt 21. In this manner, the support plate 22 is held by the belt 21. The support plate 22 has a plate shape in which at least a portion of the support plate is curved toward the inner surface side (wearing surface side). The support plate 22 is configured to include a material which is more rigid than that of the belt 21, and is configured to maintain a substantially constant shape.

The support plate 22 has a long shape or elongated shape in a longitudinal direction of the belt 21. A central portion 22a in the longitudinal direction of the support plate 22 is hardly curved, and has a flat plate shape. Both sides of the central portion 22a respectively have the first curved portion 22b (left side in FIG. 2) and a second curved portion 22c (right side in FIG. 2) which are curved toward the inner surface side and along the longitudinal direction (circumferential direction of the wrist W) of the belt 21.

Examples of materials which can be used to fabricate the support plate 22 include acrylic resin, polyvinyl chloride (particularly, rigid polyvinyl chloride), polyethylene, polypropylene, polyolefin such as polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), polyester such as polybutylene terephthalate (PBT), butadiene-styrene copolymer, aromatic or aliphatic polyamide, and fluorine-based resin such as polytetrafluoroethylene.

Similar to the belt 21, in the support plate 22, it is preferable that a portion of the support plate 22 overlapping the inflatable portion 40 is substantially transparent. However, without being limited to transparency, the portion may be translucent or colored transparent. In this manner, the puncture site P is reliably visible from the outer surface side, thereby enabling the marker 50 (to be described later) to rather easily align with the puncture site P. The support plate 22 may not have a portion which has a flat plate shape like the central portion 22a, and may be curved over the entire length.

The inflatable portion 40 functions or operates to apply a compressing force to the puncture site P after being inflated by injecting gas, and a function or operation to reduce the compressing force acting on the puncture site P with the lapse of time (i.e., over time) by discharging the injected gas outward with the lapse of time. As long as the inflatable portion 40 can be inflated, the gas injected into the inflatable portion 40 is not particularly limited. For example, air can be used.

As illustrated in FIGS. 2 and 3, the inflatable portion 40 is configured to have a bag shape by virtue of a first sheet 41 and a second sheet 42 overlapping each other.

Figure 3A:
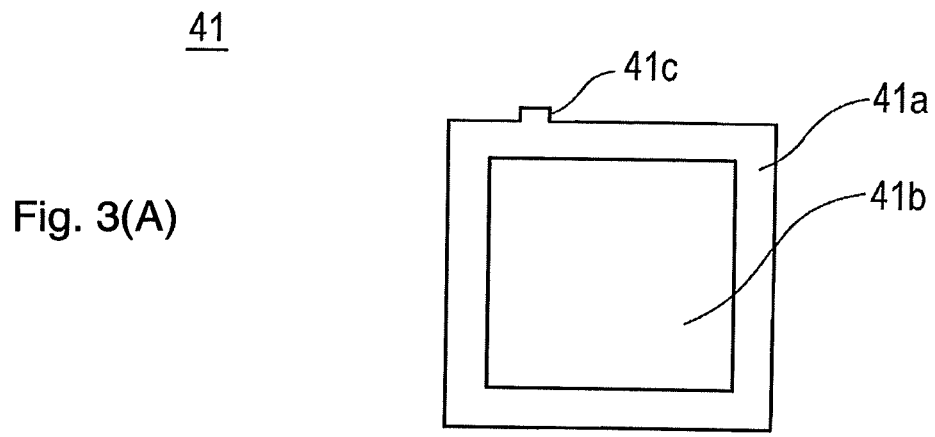
Figure 3B:
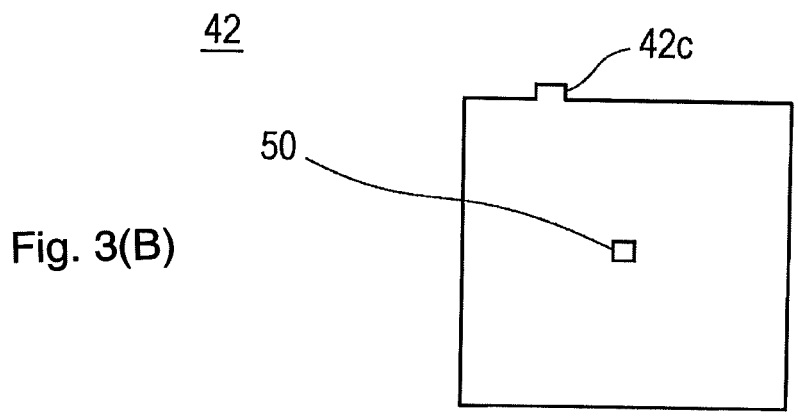
Figure 3C:
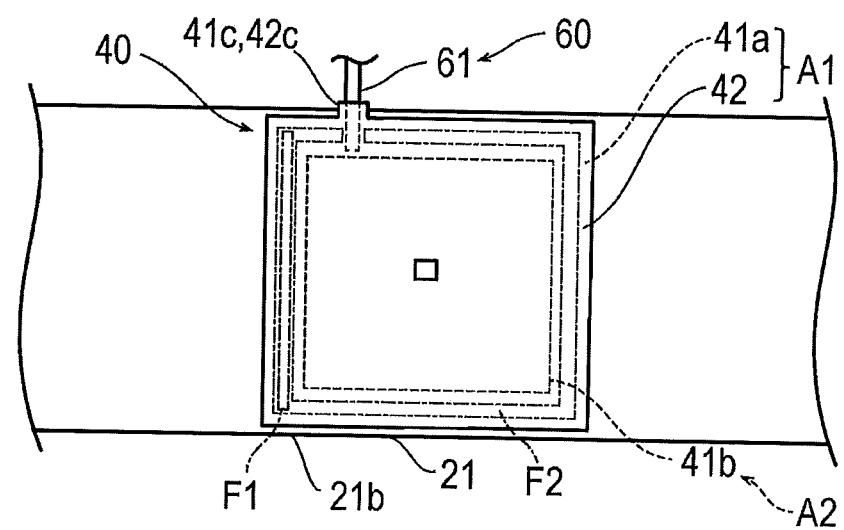
Figure 6:
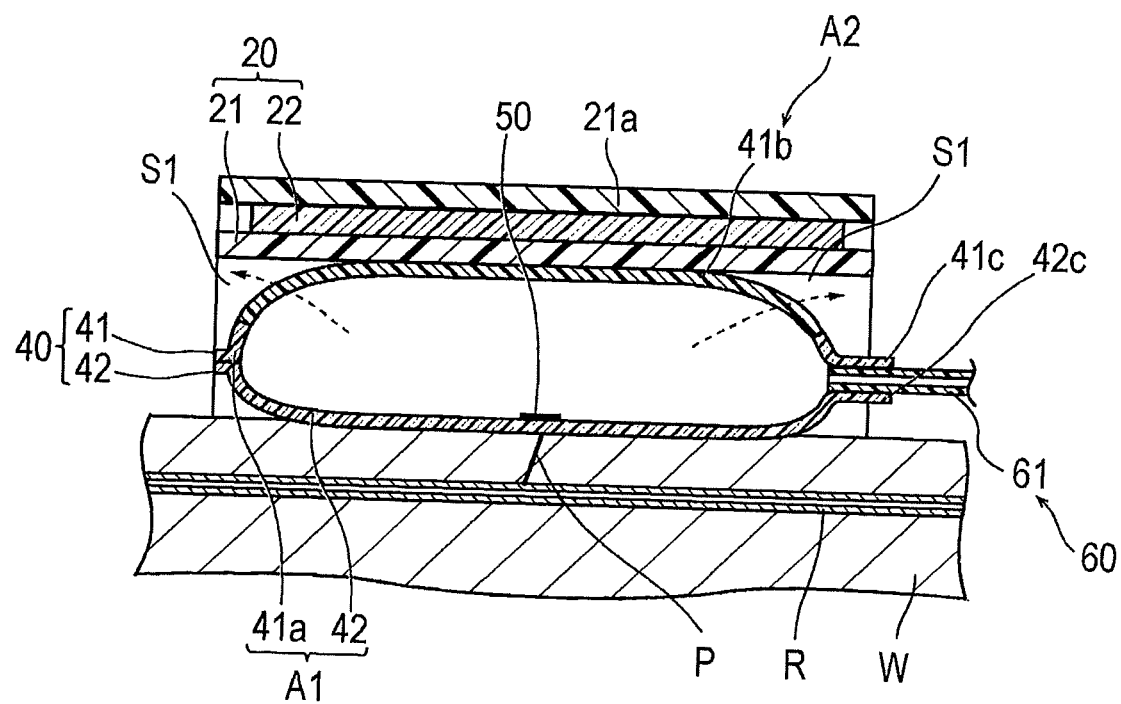
FIG. 6 is a cross-sectional view taken along the section line 6-6 in FIG. 4.

The first sheet 41 and the second sheet 42 possess a substantially rectangular outer shape in a plan view. As illustrated in FIG. 3(A), a protruding portion 41c protruding outward from a rectangular portion in a plan view is disposed in the first sheet 41. Similarly, as illustrated in FIG. 3(B), a protruding portion 42c protruding outward from a rectangular portion in a plan view is disposed in the second sheet 42. As illustrated in FIGS. 3(C) and 6, a tube 61 of the injection part 60 (to be described later) is located between the protruding portion 41c of the first sheet 41 and the protruding portion 42c of the second sheet 42. The respective protruding portions 41c and 42c adhere to the tube 61 by using an adhesive. In this manner, the tube 61 is held in the inflatable portion 40. Note that, each outer shape of the first sheet 41 and the second sheet 42 is not particularly limited to the above-described shape. For example, a circular shape, an elliptical shape, or a polygonal shape may be employed. In addition, the protruding portions 41c and 42c may not be provided.

As illustrated in FIG. 3(A), the first sheet 41 has a peripheral edge portion 41a that includes a thermoplastic material and a central portion 41b that includes a thermosetting elastomer.

According to the present embodiment, the first sheet 41 is formed as follows. The thermoplastic material and the thermosetting elastomer are respectively poured into predetermined positions of a mold having a predetermined shape, and the peripheral edge portion 41a and the central portion 41b are integrally molded. For example, the first sheet 41 may be formed as follows. The thermoplastic material is poured into the predetermined position of the mold having the predetermined shape so as to form the peripheral edge portion 41a. Thereafter, the thermosetting elastomer is poured into the predetermined position so that the peripheral edge portion 41a and the central portion 41b are integrally molded. In addition, the first sheet 41 may be formed as follows. The thermosetting elastomer is poured into the predetermined position of the mold having the predetermined shape so as to form the central portion 41b. Thereafter, the thermoplastic elastomer is poured into the predetermined position so that the peripheral edge portion 41a and the central portion 41b are integrally molded. However, the first sheet 41 may be formed as follows. A rectangular member (corresponding to the "central portion 41b") configured to include the thermosetting elastomer is located in a center of a frame-shaped member (corresponding to the "peripheral edge portion 41a") configured to include the thermoplastic material, and both of these are adhered to each other by using an adhesive.

The second sheet 42 is configured to include the thermoplastic material.

As illustrated in FIGS. 2 and 3(C), in the inflatable portion 40, a region formed of the thermoplastic material, that is, a region having the peripheral edge portion 41a (e.g., outermost peripheral edge portion) of the first sheet 41 and the second sheet 42 will be referred to as a "first region A1". In addition, in the inflatable portion 40, a region formed of the thermosetting elastomer, that is, a region having the central portion 41b of the first sheet 41 will be referred to as the "second region A2".

At least a portion of the first region A1 is welded to the interlock region 21b of the belt 21. According to the present embodiment, as illustrated in FIG. 2, the inflatable portion 40 is located in a state where the first sheet 41 faces the inner surface side of the band 20. Accordingly, one side of the peripheral edge portion 41a of the first sheet 41 and the inner surface side of the interlock region 21b of the band 20 are welded to each other. Hereinafter, a welding portion between the inflatable portion 40 and the band 20 will be referred to as a "first welding portion F1" (refer to FIG. 3(C)). In this way, the inflatable portion 40 has the first region A1 formed of the thermoplastic material. Accordingly, the first region A1 is welded to the interlock region 21b of the band 20 which is formed of the thermoplastic material. In this manner, the inflatable portion 40 and the band 20 can be interlocked with each other by welding. According to the illustrated embodiment representing one example of the disclosed hemostatic device, the first region is positioned along the outermost periphery of the one embodiment The first region Furthermore, according to the present embodiment, as illustrated in FIG. 2, an overlapping portion between the peripheral edge portion 41a of the first sheet 41 and the peripheral edge portion of the second sheet 42 is the first region A1 formed of the thermoplastic material. Therefore, as illustrated in FIG. 3(C), the overlapping portion between the peripheral edge portion 41a of the first sheet 41 and the peripheral edge portion of the second sheet 42 can be welded except for a portion into which the tube 61 of the injection part 60 (to be described later) is inserted. Hereinafter, a welding portion between the peripheral edge portion 41a of the first sheet 41 and the peripheral edge portion of the second sheet 42 will be referred to as a "second welding portion F2". The peripheral edge portion 41a of the first sheet 41 and the peripheral edge portion of the second sheet 42 may be adhered to each other by using an adhesive.

As an example of the thermoplastic material used for the first region A1, it is possible to use a thermoplastic resin such as polyvinyl chloride, polyethylene, polypropylene, and polyvinylidene chloride, or various thermoplastic elastomers such as an olefinic thermoplastic elastomer and a styrene thermoplastic elastomer. As the thermoplastic material used for the first sheet 41 and the thermoplastic material used for the interlock region 21b of the band 20, the same material is used so that a binding force in the first welding portion F1 between the first sheet 41 and the band 20 can be strengthened. However, the thermoplastic material used for the first sheet 41 and the thermoplastic material used for the interlock region 21b of the band 20 may be different from each other. In addition, as the thermoplastic material used for the first sheet 41 and the thermoplastic material used for the second sheet 42, the same material is used so that a binding force in the second welding portion F2 between the first sheet 41 and the second sheet 42 can be strengthened. However, the thermoplastic material used for the first sheet 41 and the thermoplastic material used for the second sheet 42 may be different from each other.

The thermosetting elastomer used for the second region A2 is provided with gas permeability higher than that of the thermoplastic material used for the first region A1. Therefore, as illustrated by a dotted arrow in FIGS. 5 and 6, after the inflatable portion 40 is inflated, the gas contained inside the inflatable portion 40 is discharged outward of the inflatable portion 40 via the second region A2 over time (with the lapse of time) to such an extent that vascular occlusion can be prevented. Accordingly, even if a physician or a nurse does not perform a decompressing operation, a compressing force applied to the puncture site P by the inflatable portion 40 can be reduced over time. As a result, the burden on the physician or the nurse and labor cost can be reduced. In addition, the second region A2 formed of the thermosetting elastomer has relatively high gas permeability. Accordingly, it is not necessary to excessively decrease a thickness of the inflatable portion 40 in order to increase a gas permeable amount. The strength of the inflatable portion 40 can be satisfactorily maintained. As illustrated in FIG. 5, in a case where the inflatable portion 40 has the second region A2 in the central portion 41b of the first sheet 41, it is preferable that the thickness of the second region A2 of the inflatable portion 40 is equal to or thicker than the thickness of the first region A1 of the inflatable portion 40. In this manner, on an outer surface of the inflatable portion 40, a concave portion is not formed in the vicinity of a boundary between the first region A1 and the second region A2. Accordingly, sweat or a foreign substance is less likely to be accumulated in the second region A2 of the outer surface of the inflatable portion 40. Therefore, the second region A2 of the inflatable portion 40 can suitably maintain the gas permeability.

A gas permeability coefficient of the thermosetting elastomer used for the second region A2 is preferably equal to or higher than 10 times the gas permeability coefficient of the thermoplastic material used for the first region A1. That is, the gas permeability coefficient of the thermosetting elastomer used for the second region A2 is preferably at least 10 times greater than the gas permeability coefficient of the thermoplastic material used for the first region A1. More preferably the gas permeability coefficient of the thermosetting elastomer used for the second region A2 is equal to or higher than 100 times, and much more preferably equal to or higher than 1,000 times, the gas permeability coefficient of the thermoplastic material used for the first region A1. In this manner, the hemostatic device 10 can suitably adjust the compressing force applied to the puncture site P by the inflatable portion 40 so as to be reduced over time by using a difference in the gas permeability coefficient between the first region A1 and the second region A2. In addition, from a viewpoint of the gas permeability coefficient, the thermoplastic material used for the first region A1 is preferably a thermoplastic resin. in the description herein, the gas permeability coefficient means a permeability coefficient of mixed gas of oxygen and nitrogen (volume ratio of oxygen to nitrogen, oxygen:nitrogen=20:80).

In addition, in order to obtain a sufficient hemostasis effect, it is preferable that a state of compressing the puncture site P is maintained by the inflatable portion 40 at least for 4 hours after the inflatable portion 40 is inflated. In addition, in order to prevent the vascular occlusion while the puncture site P is compressed, it is preferable that internal pressure of the inflatable portion 40 is reduced with the passage of time so as to reduce the compressing force applied to the puncture site P by the inflatable portion 40 over time. In order that the compressing force acting on the puncture site P is changed with the passage of time to the same extent when the decompressing operation is performed using a dedicated instrument such as a syringe in the related art, it is preferable to set a type, a thickness, and a surface area of the thermosetting elastomer of the second region A2 so as to satisfy the following two conditions:

(Condition 1) In a state where the band 20 is wrapped around the wrist W, the gas should preferably be discharged outward of the inflatable portion 40 via the second region A2 over 4 hours after the inflatable portion 40 is inflated. After every one hour elapses, the internal pressure of the inflatable portion 40 reaches 70% to 97% (preferably, 75% to 94%) of the internal pressure of the inflatable portion 40 one hour ago;

(Condition 2) In a state where the band 20 is wrapped around the wrist W, the internal pressure inside the inflatable portion 40 after 4 hours elapses from when the inflatable portion 40 is inflated reaches 30% to 80% (preferably, 40% to 71%) of the initial internal pressure.

Condition 1 and Condition 2 may be substituted with Condition 3 and Condition 4 below:

(Condition 3) In a state where the band 20 is wrapped around the wrist W, the gas should preferably be discharged outward of the inflatable portion 40 via the second region A2 over 4 hours after the inflatable portion 40 is inflated. After every one hour elapses, a volume of the gas injected into the inflatable portion 40 reaches 85% to 96% (preferably, 88% to 96%) of a volume of the gas inside the inflatable portion 40 one hour ago;

(Condition 4) In a state where the band 20 is wrapped around the wrist W, the volume of the gas inside the inflatable portion 40 after 4 hours elapses from when the inflatable portion 40 is inflated reaches 55% to 95% (preferably, 60% to 80%) of the initial volume of the gas inside the inflatable portion 40.

In order to satisfy Condition 1 and Condition 2 (or Condition 3 and Condition 4) described above, it is necessary to appropriately set the thickness and the surface area of the second region A2. However, in view of a fact that a film thickness of the inflatable portion is generally approximately 0.5 mm and a total surface area is approximately 16 $cm^2$, it is possible to form the second region A2 by using the thermosetting elastomer whose gas permeability coefficient is 75 to $550 \times 10^{-8}$ cc·cm/$cm^2$·sec·atm (preferably, 200 to $400 \times 10^{-8}$ cc·cm/$cm^2$·sec·atm). For example, this material includes silicone rubber.

In this way, the inflatable portion 40 includes not only the second region A2 formed of the thermosetting elastomer, but also the first region A1 formed of the thermoplastic material. Therefore, after the inflatable portion 40 is inflated, the gas contained inside the inflatable portion 40 can be discharged out of the inflatable portion 40 via the second region A2 formed of the thermosetting elastomer with the passage of time to such an extent that the vascular occlusion can be prevented. The first region A1 and the interlock region 21b are welded to each other, thereby enabling the inflatable portion 40 and the band 20 to be strongly interlocked with each other by the welding.

As described above, the inflatable portion 40 is located on the inner surface side of the band 20. Therefore, if the inflatable portion 40 is inflated, the inflation of the inflatable portion 40 in a direction away from the body surface side of the wrist W is suppressed by the band 20. In this manner, the compressing force of the inflatable portion 40 can be concentrated on the wrist W side, and the compressing force can be suitably applied to the puncture site P. In addition, the inflatable portion 40 is pressed on the wrist W by the band 20 so as to increase the internal pressure. Accordingly, the gas contained inside the inflatable portion 40 can be suitably discharged outward. Furthermore, it is possible to suitably prevent the discharge of the gas contained inside the inflatable portion 40 from being hindered in such a way that a patient wearing the hemostatic device 10 inadvertently touches the second region A2.

In addition, if a surface of the inflatable portion 40 which is located on the wrist W side is defined as a "first surface" (second sheet 42 side) and a surface located on the band 20 side is defined as a "second surface" (first sheet 41 side), according to the present embodiment, the second region A2 formed of the thermosetting elastomer is disposed in the central portion of the second surface. Then, a peripheral edge portion surrounding the central portion of the second surface is configured to include the thermoplastic material. Therefore, the central portion of the second region A2 is most likely to stretch, and the peripheral edge portion of the second region A2 is pulled by the thermoplastic material which is relatively less likely to stretch. Accordingly, the peripheral edge portion of the second region A2 is less likely to stretch, compared to the central portion of the second region A2. Therefore, as illustrated in FIG. 5, if the inflatable portion 40 is inflated, the central portion of the second region A2 bulges most to the band 20 side, and the peripheral edge portion of the second region A2 is separated from the band 20, thereby forming a space S1 between the peripheral edge portion of the second region A2 and the band 20. Therefore, in the inflatable portion 40, a portion exposed without coming into contact with the band 20 in the second region A2 can be secured, and the gas can be suitably discharged outward of the inflatable portion 40 from the exposed portion. In addition, when the inflatable portion 40 is inflated, in the inflatable portion 40, the center of the inflatable portion 40 located at a position facing the puncture site P bulges most. Accordingly, the puncture site P can be satisfactorily compressed. In addition, the second region A2 formed of a material different from a material configuring the belt 21 of the band 20 is disposed on the second surface located on the band 20 side. In this manner, the belt 21 and the inflatable portion 40 or the first surface of the inflatable portion 40 and the second surface of the inflatable portion 40 can be suitably prevented from being adsorbed due to an intermolecular force.

It is preferable that the inflatable portion 40 is substantially transparent. However, without being limited to transparency, the inflatable portion may be translucent or colored transparent. In this manner, the puncture site P is visible from the outer surface side, thereby enabling the marker 50 (to be described later) to easily align with the puncture site P.

As illustrated in FIG. 2, the marker 50 is disposed in substantially the center of the first surface side (substantially the center of the second sheet 42) located on the wrist W side, on the inner surface of the inflatable portion 40. Since this marker 50 is disposed in the inflatable portion 40, the inflatable portion 40 can be rather easily aligned with the puncture site P. Accordingly, misalignment of the inflatable portion 40 is suppressed. In addition, the marker 50 is disposed in the second sheet 42 configuring the first region A1. Accordingly, the marker 50 does not hinder the gas permeability in the second region A2. In addition, the marker 50 is disposed on the inner surface side of the inflatable portion 40. Accordingly, the marker 50 does not come into direct contact with the puncture site P. The position for the marker 50 is not particularly limited, as long as the inflatable portion 40 can be aligned with the puncture site P. For example, the marker 50 may be disposed in substantially the center (substantially the center of the first sheet 41) of the second surface side located on the band 20 side in the inflatable portion 40.

A shape of the marker 50 is not particularly limited. For example, a circular shape, a triangular shape, or a quadrangular shape may be employed. According to the present embodiment, the quadrangular shape is employed.

A size of the marker 50 is not particularly limited. However, for example, in a case where the shape of the marker 50 is the quadrangular shape, it is preferable that a length of one side of the marker 50 falls within a range of 1 to 4 mm. If the length of one side is 5 mm or longer, the size of the marker 50 is larger than the size of the puncture site P. Accordingly, the central portion of the inflatable portion 40 is less likely to align with the puncture site P.

Without being particularly limited, a material of the marker 50 includes oily colorants such as ink, and resins kneaded with pigments.

A color of the marker 50 is not particularly limited, as long as the color enables the inflatable portion 40 to align with the puncture site P. However, it is preferable that the color is a green color system. Since the green color system is used, the marker 50 is easily visible on the blood or the skin. Accordingly, the inflatable portion 40 is much likely to align with the puncture site P.

In addition, it is preferable that the marker 50 is translucent or colored transparent. In this manner, the puncture site P is visible from the outer surface side of the marker 50.

A method of disposing the marker 50 at the inflatable portion 40 is not particularly limited. As an example, the method may involve a method of printing the marker 50 on the inflatable portion 40, and a method of attaching the marker 50 to the inflatable portion 40 by applying an adhesive to one side surface of the marker 50. In addition, in a case where the marker 50 is disposed in the first region A1, the marker 50 can be attached thereto by the welding.

The injection part 60 is used for injecting the gas into the inflatable portion 40. As illustrated in FIG. 1, the injection part 60 is connected to the inflatable portion 40.

A proximal portion of the injection part 60 is connected to the inflatable portion 40. The injection part 60 includes the flexible tube 61 whose lumen communicates with the inside of the inflatable portion 40, a bag 62 which is located in a distal portion of the tube 61 so as to communicate with the lumen of the tube 61 and which has a check valve (not illustrated) incorporated therein, and a tubular connector 63 connected to the bag 62.

As illustrated in FIG. 3(C), the tube 61 is connected to the inflatable portion 40 so as to be interposed between the protruding portion 41c of the first sheet 41 and the protruding portion 42c of the second sheet 42. However, a position for connecting the tube 61 in the inflatable portion 40 is not particularly limited, as long as the lumen of the tube 61 communicates with an internal space of the inflatable portion 40.

When the inflatable portion 40 is inflated (expanded), a distal tubular portion of a syringe is inserted into the connector 63 so as to open the check valve. A plunger of the syringe is pressed, and the gas contained inside the syringe is injected into the inflatable portion 40 via the injection part 60. If the inflatable portion 40 is inflated, the bag 62 communicating with the inflatable portion 40 via the tube 61 is expanded. It is possible to visually confirm that the inflatable portion 40 can be pressurized without leakage of the gas. If the distal tubular portion of the syringe is removed from the connector 63 after the gas is injected into the inflatable portion 40, the check valve incorporated in the connector 63 is closed, thereby preventing the leakage of the gas.

Next, a method of using the hemostatic device 10 according to the present embodiment will be described.

Before the hemostatic device 10 is worn on the wrist W, the inflatable portion 40 is in a non-inflated state as illustrated in FIG. 2. As illustrated in FIGS. 4 and 5, in a case where the radial artery R of the wrist W of the right hand is punctured, the puncture site P is located at a position close to a thumb side. Normally, the introducer sheath indwells the puncture site P. The band 20 is wrapped around the wrist W in a state where the introducer sheath indwells the puncture site P. That is, the band 20 is applied to the wrist while the introducer sheath remains indwelled at the puncture site P. The inflatable portion 40 and the band 20 are so aligned that the marker 50 disposed in the inflatable portion 40 overlaps the puncture site P from above. The male side 31 and the female side 32 of the surface fastener 30 are brought into contact with and joined to each other. In this manner, the band 20 is worn on the wrist W.

In this case, the hemostatic device 10 is worn on the wrist W so that the injection part 60 faces a downstream side (palm side) of a blood flow in the radial artery R. In this manner, the injection part 60 can be operated without interfering with a medical procedure on an upstream side from the wrist or an instrument (for example, a blood pressure monitor) located on the upstream side. In addition, the hemostatic device 10 is worn on the wrist W of the right hand so that the injection part 60 faces a downstream side. In this manner, the inflatable portion 40 is located in the radial artery R located close to the thumb side of the wrist W. In a case of an artery, the upstream side of the blood vessel indicates a direction closer to a heart of the blood vessel. In addition, the downstream side of the blood vessel indicates a direction farther away from the heart of the blood vessel.

The hemostatic device 10 may be used in a case where the radial artery of the wrist of a left hand is punctured. In this case, the hemostatic device 10 is worn on the wrist W of the left hand so that the injection part 60 faces the upstream side of the blood flow in the radial artery.

After the hemostatic device 10 is worn on the wrist W, a syringe is connected to the connector 63 of the injection part 60. As described above, the gas is injected into the inflatable portion 40 so as to inflate the inflatable portion 40.

In this case, an injection amount of the gas is adjusted in accordance with a clinical case. In this manner, an inflated degree of the inflatable portion 40, that is, the compressing force acting on the puncture site P can be easily adjusted. For example, in a case where the inflatable portion 40 is excessively inflated since the gas is excessively injected into the inflatable portion 40, the excessively injected gas may be discharged from the inside of the inflatable portion 40 by using the syringe. As described above, since the second region A2 of the inflatable portion 40 is formed of the thermosetting elastomer, the second region A2 is elastic. Therefore, if the gas excessively injected into the inflatable portion 40 is discharged outward, the inflatable portion 40 is deflated and deformed in response to the discharge. The inflatable portion 40 comes to have a desired inflated degree, and can apply the suitable compressing force to the puncture site P.

After the inflatable portion 40 is inflated, the syringe is separated from the connector 63. Then, the introducer sheath is removed from the puncture site P.

After the inflatable portion 40 is inflated, as illustrated by arrows in FIGS. 5 and 6, the gas contained inside the inflatable portion 40 is discharged outward of the inflatable portion 40 via the second region A2 over time to such an extent that the vascular occlusion can be prevented.

In a case where the hemostasis is not sufficiently performed after the inflatable portion 40 is inflated, the internal pressure of the inflatable portion 40 may be increased by injecting gas into the inflatable portion 40. For example, in a case where the internal pressure of the inflatable portion 40 needs to return to the internal pressure maintained when the gas is injected into the inflatable portion 40, the gas may be injected as much as the amount discharged from the inflatable portion 40.

After a predetermined period of time elapses and the hemostasis of the puncture site P is completely performed, the hemostatic device 10 is detached from the wrist W. The hemostatic device 10 is detached from the wrist W by separating the male side 31 and the female side 32 of the surface fastener 30 from each other.

In a case where unlike the hemostatic device 10 of the present embodiment, the inflatable portion is configured to include a material that stretches over time, immediately after the inflatable portion is inflated, the inflatable portion is gradually inflated and deformed. This deformation is plastic deformation. Accordingly, in a case where the inflatable portion is excessively inflated, even if the excessively injected gas is discharged outward, the inflatable portion is less likely to be correspondingly deflated. The internal pressure of the inflatable portion is lower than desired internal pressure. Therefore, in a case where the inflatable portion is excessively inflated, it is necessary to appropriately adjust the amount of the gas to be discharged in accordance with a stretching state of the inflatable portion. As described above, in the hemostatic device 10 according to the present embodiment, if the amount of the excessively injected gas is discharged, the internal pressure of the inflatable portion 40 can be adjusted to the desired pressure. Accordingly, when the inflatable portion 40 is excessively inflated, treatment can be more easily performed.

In addition, in a case where the inflatable portion is configured to include material that stretches over time, when the hemostasis is insufficiently performed after a certain period of time elapses from when the inflating portion is inflated and the gas is further injected into the inflatable portion in order to increase the internal pressure of the inflatable portion, the inflatable portion is further inflated and deformed. Therefore, the thickness of the inflatable portion becomes much thinner. In addition, a contact area between the inflatable portion and the wrist is further increased. Accordingly, nerves around the puncture site P are likely to be compressed, and a wearer is likely to feel numbness or pain. The compressing force is scattered, and does not concentrate on the puncture site P. Therefore, it is considered that the hemostasis effect is relatively reduced. In addition, unlike the hemostatic device 10 according to the present embodiment, even if the gas is injected as much as the amount discharged from the inflatable portion 40, the inflatable portion does not return to the initial state. It is necessary to appropriately adjust the amount of the gas to be injected in accordance with a stretching state of the inflatable portion. Therefore, the hemostatic device 10 according to the present embodiment can more easily perform the treatment when the gas is injected into the inflatable portion again.

As described above, the hemostatic device 10 according to the present embodiment includes the band 20 for being wrapped around the puncture site P of the wrist W, the means 30 for securing the band 20 in a state of being wrapped around the wrist W, and the inflatable portion 40 that interlocks with the band 20, and that is inflated by injecting the gas so as to compress the puncture site P. The inflatable portion 40 has the first region A1 formed of the thermoplastic material and the second region A2 formed of the thermosetting elastomer whose gas permeability is higher than that of the thermoplastic material. The band 20 has the interlock region 21b that is formed of the thermoplastic material, and that interlocks with the inflatable portion 40. The first region A1 of the inflatable portion 40 is welded to the interlock region 21b of the band 20.

According to the hemostatic device 10 configured in this way, after the inflatable portion 40 is inflated, the gas contained in the inflatable portion 40 is discharged outward of the inflatable portion 40 via the second region A2 formed of the thermosetting elastomer with the lapse of time to such an extent that the vascular occlusion can be prevented. In this case, the second region A2 formed of the thermosetting elastomer has relatively high gas permeability. Accordingly, it is not necessary to excessively decrease the thickness of the inflatable portion 40 in order to increase the gas permeable amount. Therefore, the strength of the inflatable portion 40 can be satisfactorily maintained, and without operation by a physician or a nurse, the compressing force acting on the puncture site P can be reduced with the lapse of time to such an extent that the vascular occlusion can be prevented. Furthermore, the first region A1 formed of the thermoplastic material is disposed in the inflatable portion 40, and the interlock region 21b formed of the thermoplastic material is disposed in the band 20. Therefore, the first region A1 and the interlock region 21b are welded to each other. In this manner, it is possible to provide the hemostatic device 10 in which the inflatable portion 40 and the band 20 are interlocked with each other.

In addition, the inflatable portion 40 is located on the side facing the wrist W in the band 20. Therefore, the band 20 presses the inflatable portion 40 against the wrist W, and the internal pressure of the inflatable portion 40 increases, thereby enabling the gas contained inside the inflatable portion 40 to be more suitably discharged.

In addition, the band 20 is configured to include a material whose elastic modulus is higher than that of the second region A2. Therefore, the band 20 is relatively less likely to stretch, and the inflatable portion 40 can be pressed against the wrist W without being significantly affected by a size of a patient's wrist. In this manner, the internal pressure of the inflatable portion 40 increases, and thus, the gas contained inside the inflatable portion 40 can be more suitably discharged.

In addition, in a state where the band 20 is wrapped around the wrist W, the inflatable portion 40 has the first surface located on the wrist W side and the second surface located on the band 20 side. At least a portion of the second region A2 is disposed in the central portion of the second surface. Therefore, the central portion of the second region A2 bulges most to the band 20 side, and the peripheral edge portion of the second region A2 is separated from the band 20, thereby forming the space S1 between the second region A2 of the inflatable portion 40 and the band 20. Therefore, the portion exposed from the band 20 can be secured in the second region A2, and the gas contained inside the inflatable portion 40 can be satisfactorily discharged from the exposed portion. Furthermore, the central portion of the inflatable portion 40 located at the position facing the puncture site P bulges most. Accordingly, the puncture site P can be suitably compressed.

In addition, the second region A2 is formed of the thermosetting elastomer whose gas permeability coefficient is 75 to 550×10$^{-8}$ cc·cm/cm$^2$·sec·atm. Therefore, similar to a case of performing the decompressing operation using the dedicated instrument such as the syringe in the related art, while a compressing time of approximately 4 hours is ensured, the compressing force acting on the puncture site P can be reduced with the passage of time.

The thermosetting elastomer used for the second region may be silicone rubber. The gas permeability coefficient of silicone rubber is approximately 240×10$^{-8}$ cc·cm/cm$^2$·sec·atm. Therefore, to the same extent when the decompressing operation is performed using the dedicated instrument such as the syringe in the related art, while the compressing time of approximately 4 hours is ensured, the compressing force acting on the puncture site P can be reduced over time.

Modification Example 1

Figure 7:
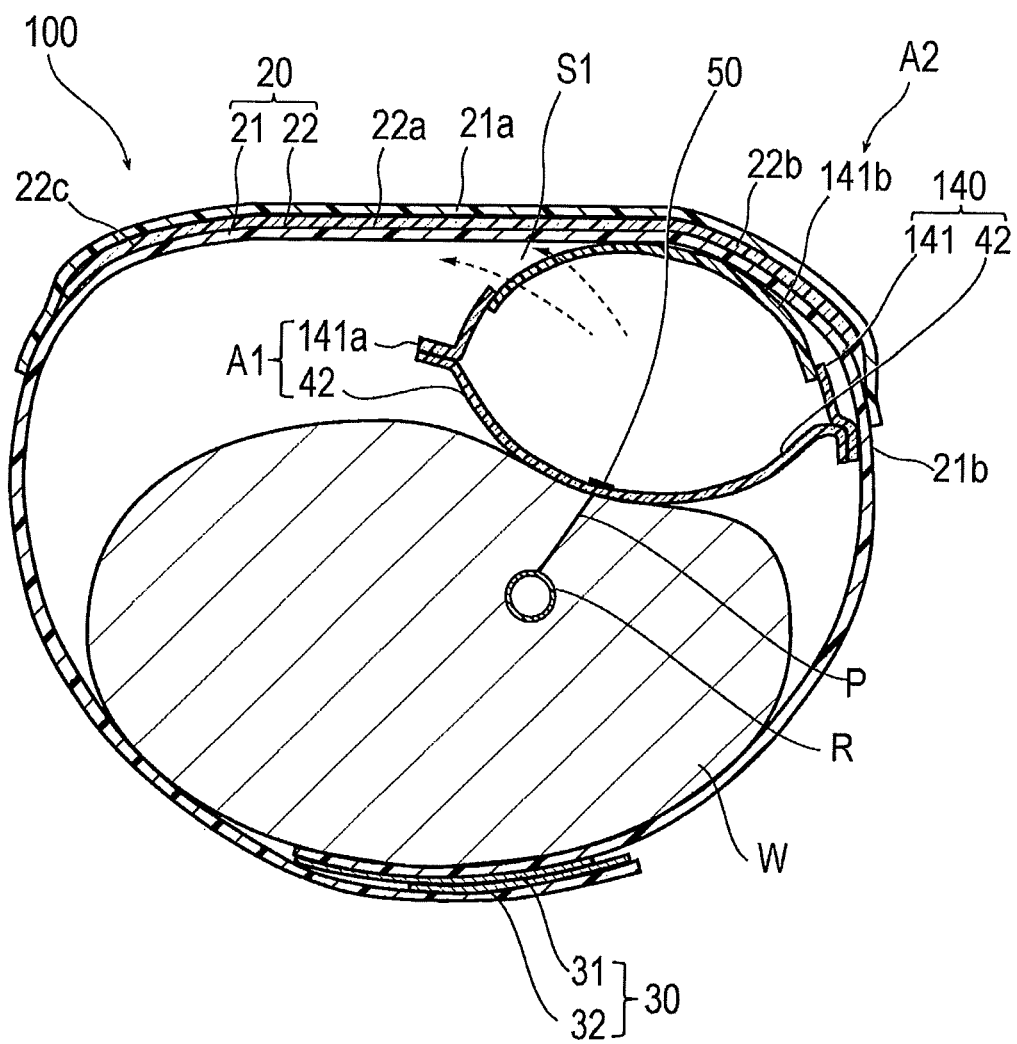
FIG. 7 is a cross-sectional view illustrating a hemostatic device according to Modification Example 1.

FIG. 7 is a view illustrating a hemostatic device 100 according to Modification Example 1. In the description which follows, features that are the same or similar to those described above are identified by common reference numerals and a detailed description of such features is not repeated.

An inflatable portion 140 included in the hemostatic device 100 according to Modification Example 1 is different from the above-described embodiment in a configuration of a first sheet 141.

The first sheet 141 has a peripheral edge portion 141a formed of the thermoplastic material and a central portion 141b formed of the thermosetting elastomer. The central portion 141b is attached to the inner surface side (internal space side of the inflatable portion 140) of the peripheral edge portion 141a so as to overlap the peripheral edge portion 141a.

According to the hemostatic device 100 in Modification Example 1 described above, the central portion 141b formed of the thermosetting elastomer is attached to the inner surface side of the peripheral edge portion 141a so as to overlap the peripheral edge portion 141a. Therefore, when the inflatable portion 140 is inflated, the central portion 141b of the inflatable portion 140 which bulges most is held so as to be pressurized by the peripheral edge portion 141a. As a result, when the inflatable portion 140 is inflated, it is possible to suitably prevent the central portion 141b from being separated from the peripheral edge portion 141a by receiving the internal pressure of the inflatable portion 140.

The central portion 141b formed of the thermosetting elastomer may be configured so as not to have a step difference with the peripheral edge portion 141a of the first region A1, on the outer surface of the inflatable portion 140. For example, the thickness of a portion of the central portion 141b formed of the thermosetting elastomer may be equal to or thicker than the thickness of the first region A1 so that there is no step difference with the peripheral edge portion 141a of the first region A1. In this manner, a concave portion is not formed in the vicinity of a boundary between the first region A1 and the second region A2 on the outer surface of the inflatable portion 140. Accordingly, sweat or a foreign substance is less likely to be accumulated in the second region A2 of the outer surface of the inflatable portion 140. Therefore, the second region A2 of the inflatable portion 140 can suitably maintain the gas permeability.

Modification Example 2

Figure 8:
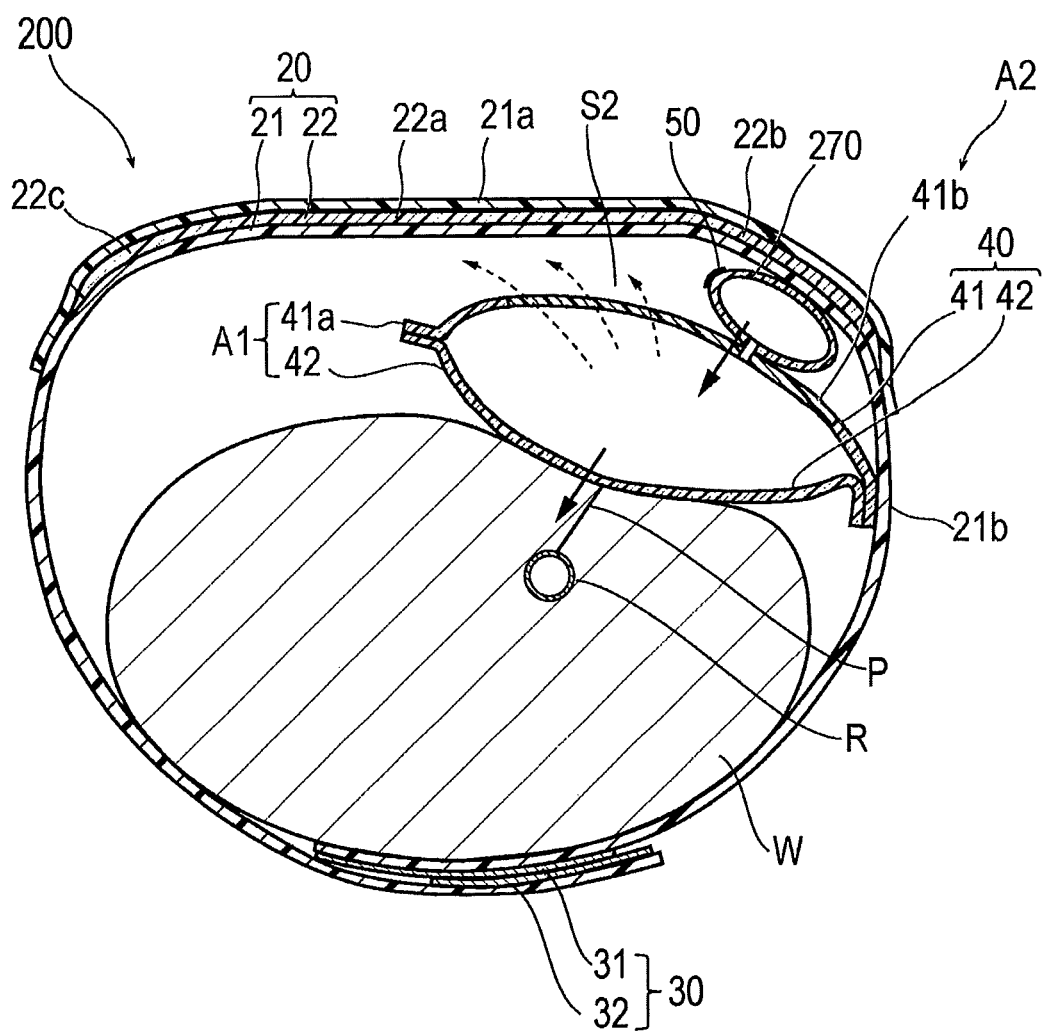
FIG. 8 is a cross-sectional view illustrating a hemostatic device according to Modification Example 2.

FIG. 8 is a view illustrating a hemostatic device 200 according to Modification Example 2. In the following description, features that are the same or similar to those described above are identified by common reference numerals and a detailed description of such features is not repeated.

The hemostatic device 200 according to Modification Example 2 is different from the above-described embodiment in that an auxiliary compression portion 270 is provided between the inflatable portion 40 and the band 20, and in that the marker 50 is disposed in the auxiliary compression portion 270.

The auxiliary compression portion 270 is formed in a bag shape similar to that of the inflatable portion 40. The auxiliary compression portion 270 is attached to the inflatable portion 40 so that the internal space of the auxiliary compression portion 270 communicates with the internal space of the inflatable portion 40. Therefore, if the gas is injected into the inflatable portion 40, the auxiliary compression portion 270 is also inflated. The auxiliary compression portion 270 may be configured to include a sponge-like substance, an elastic material, an aggregate of fibers such as cotton, or a combination thereof.

The marker 50 is disposed in an end portion on a side close to the center of the inflatable portion 40, on the outer surface of the auxiliary compression portion 270. Since this marker 50 is disposed in the auxiliary compression portion 270, the inflatable portion 40 can be rather easily aligned with the puncture site P. Accordingly, misalignment of the inflatable portion 40 is suppressed. In addition, since the marker 50 is disposed in the auxiliary compression portion 270, the gas permeation in the second region A2 of the inflatable portion 40 is not hindered. A position for providing the marker 50 is not particularly limited, as long as the inflatable portion 40 can be aligned with the puncture site P. For example, the marker 50 may be disposed on the inflatable portion 40 side.

According to the hemostatic device 200 in Modification Example 2 described above, as illustrated by a solid arrow in FIG. 8, a direction of the compressing force applied by the inflatable portion 40 can be adjusted to a direction oriented toward the puncture site P by the auxiliary compression portion 270. In addition, since the auxiliary compression portion 270 is provided, a larger space S2 between the second region A2 of the inflatable portion 40 and the band 20 can be secured compared to the above-described embodiment. It is possible to increase an area of a portion exposed without coming into contact with the band 20 in the second region A2. Therefore, the gas can be more satisfactorily discharged from the exposed portion.

Modification Example 3

FIG. 9 is a view illustrating a hemostatic device 300 according to Modification Example 3. In the description which follows, features that are the same or similar to those described above are identified by common reference numerals and a detailed description of such features is not repeated.

The hemostatic device 300 according to Modification Example 3 is different from that according to the above-described embodiment in that the hemostatic device 300 includes a sealing member 380 including a material whose gas permeability is lower than that of the second region A2 and detachably covering the outer surface of the second region A2.

Figure 9A:
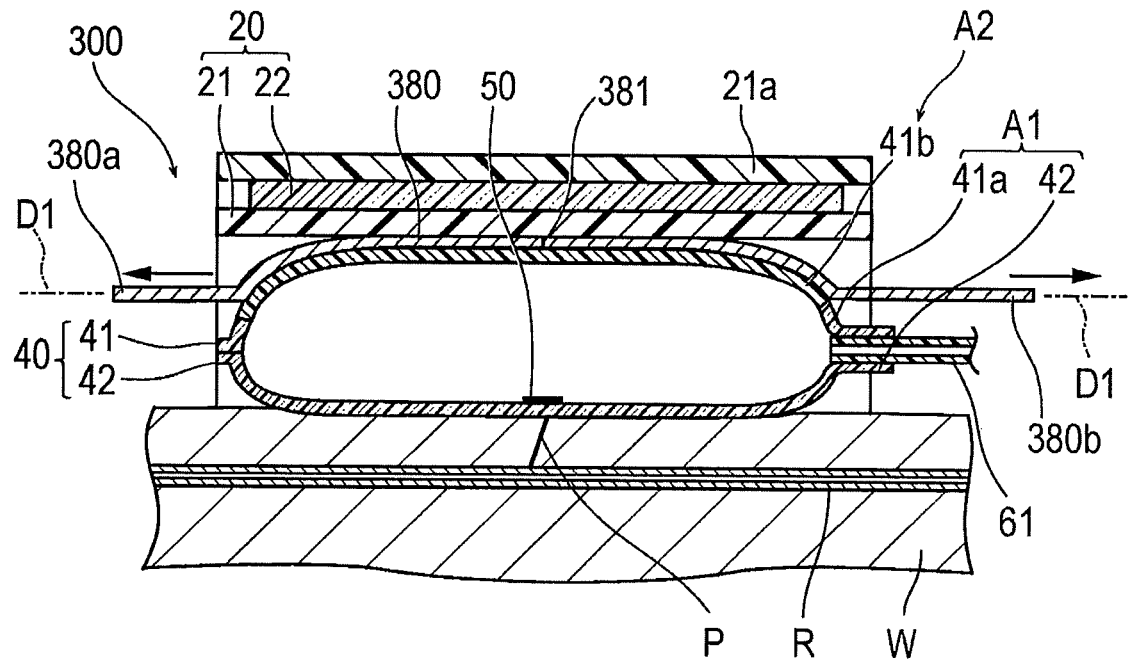
FIGS. 9(A) and 9(B) are cross-sectional views illustrating a hemostatic device according to Modification Example 3.

As illustrated in FIG. 9(A), the sealing member 380 is disposed so as to cover the outer surface of the second region A2. In addition, two end portions 380a and 380b extending along the longitudinal direction of the band 20 in the sealing member 380 respectively protrude outward from the band 20 along a direction D1 intersecting the longitudinal direction of the band 20.

A breakable portion 381 which is easily broken when the respective end portions 380a and 380b are pulled in a direction away from the band 20 (direction indicated by the arrows in FIG. 9(A)) is disposed between the two end portions 380a and 380b. For example, the breakable portion 381 may be formed by disposing a cutout portion in the sealing member 380 at a predetermined interval along the longitudinal direction of the band 20, or may be formed by decreasing the thickness of a portion of the sealing member 380.

Figure 9B:
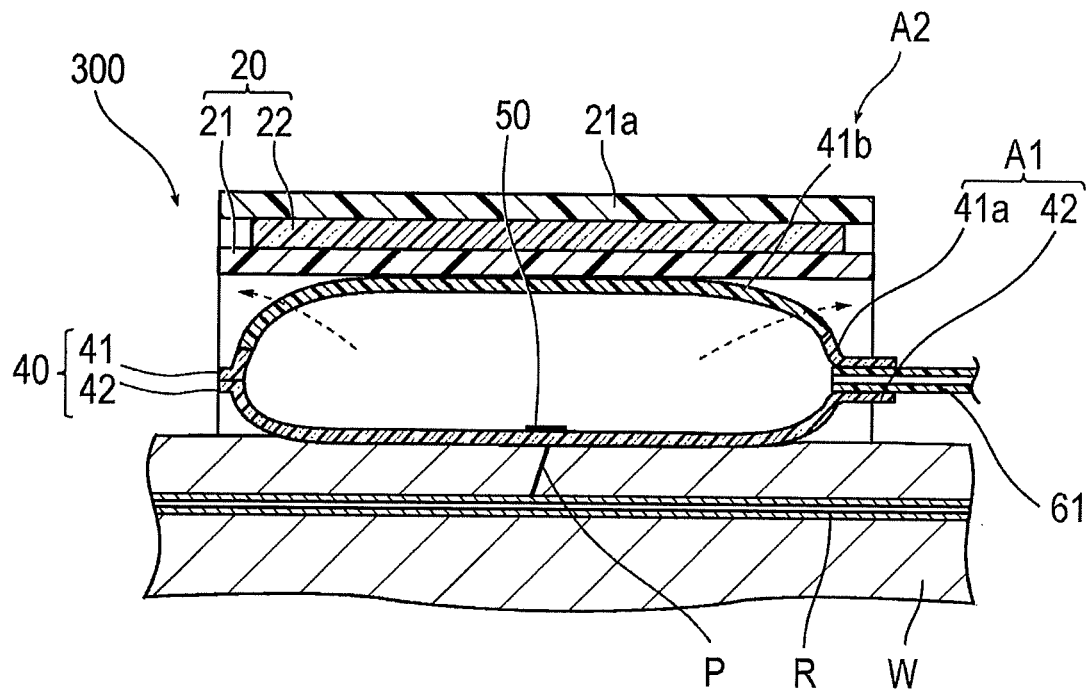

After the hemostatic device 300 is attached to the wrist W and the inflatable portion 40 is inflated, if the two end portions 380a and 380b of the sealing member 380 are respectively pulled in a direction away from the band 20, the sealing member 380 is broken at the breakable portion 381 and may be removed. Accordingly, the second region A2 is exposed as illustrated in FIG. 9(B). In this way, the sealing member 380 is removed by pulling the two end portions 380a and 380b in mutually opposite directions. Accordingly, compared to a case where the sealing member 380 is pulled in one direction, it is possible to suitably prevent the inflatable portion 40 from being misaligned with the puncture site P after being pulled by the operation of removing the sealing member 380.

The material forming the sealing member 380 is not particularly limited, as long as the material has the gas permeability lower than that of the second region A2. However, it is preferable that the material also has the gas permeability equal to or lower than that of the first region A1. As an example of such a material, it is possible to use a gas barrier film such as a transparent film on which silica is subjected to vapor deposition on a plastic film. In this way, the sealing member 380 is configured to include a transparent member. Accordingly, even in a state where the sealing member 380 is disposed in the inflatable portion 40, the puncture site P is visible from the outer surface side, and the marker 50 can easily align with the puncture site P.

According to the hemostatic device 300 in Modification Example 3 described above, at least a portion of the outer surface of the second region A2 is detachably covered with the sealing member 380 whose gas permeability is lower than that of the second region A2. Therefore, a timing for detaching the sealing member 380 is adjusted, thereby enabling the gas to be discharged via the second region A2 at any desired timing.

Modification Example 4

Figure 10:
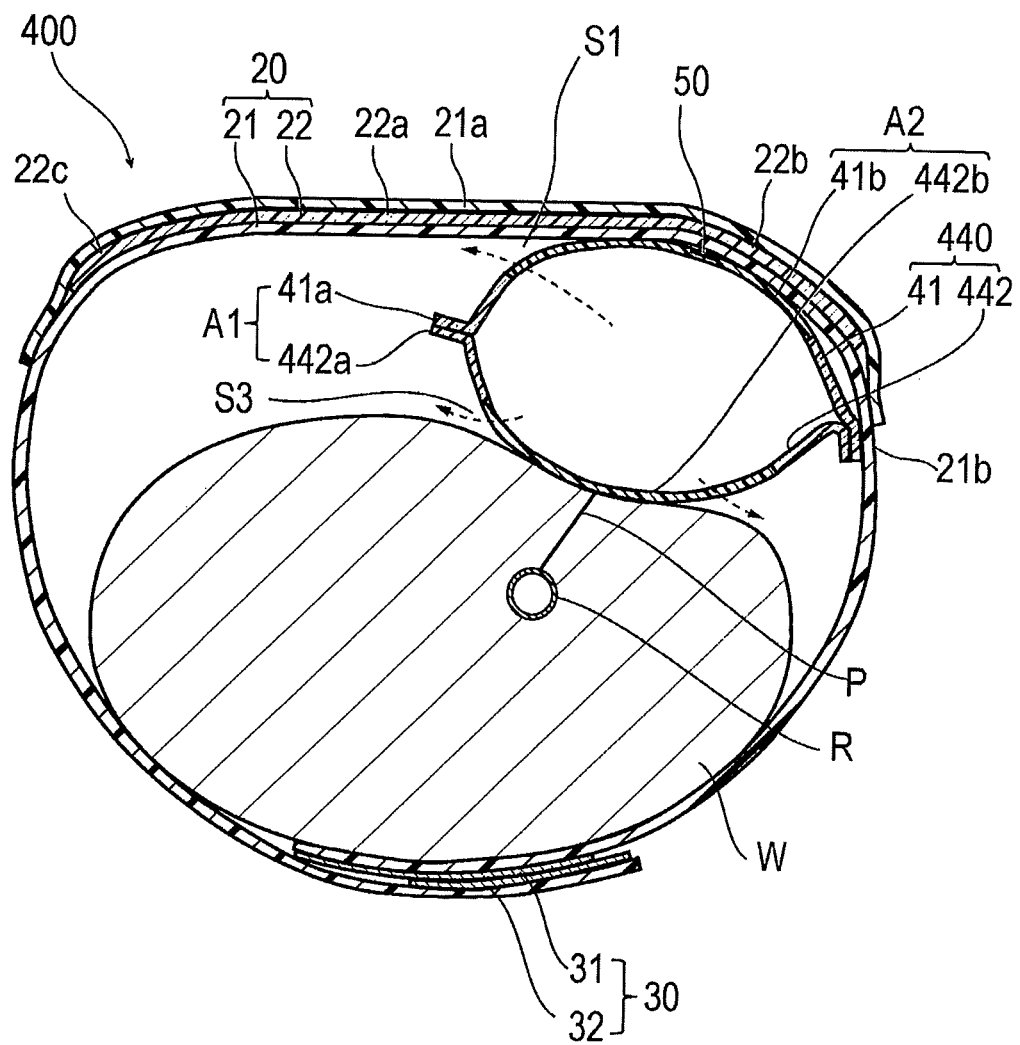
FIG. 10 is a cross-sectional view illustrating a hemostatic device according to Modification Example 4.

FIG. 10 is a view illustrating a hemostatic device 400 according to Modification Example 4. In the following description, features that are the same or similar to those described above are identified by common reference numerals and a detailed description of such features is not repeated.

The hemostatic device 400 according to Modification Example 4 is different from that according to the above-described embodiment in that a second sheet 442 configuring an inflatable portion 440 has a peripheral edge portion 442a configured to include the thermoplastic material and a central portion 442b configured to include the thermosetting elastomer, and in that the marker 50 is disposed on the second surface side located on the band 20 side, in the inflatable portion 440.

Therefore, in the hemostatic device 400 according to Modification Example 4, in the inflatable portion 440, a region having the peripheral edge portion 41a of the first sheet 41 and the peripheral edge portion 442a of the second sheet 442 corresponds to the first region A1. In addition, in the hemostatic device 400 according to Modification Example 4, in the inflatable portion 440, a region having the central portion 41b of the first sheet 41 and the central portion 442b of the second sheet 442 corresponds to the second region A2.

In addition, a material of the second region A2 is not limited as long as it is a thermosetting elastomer, as in the above-described embodiment. However, particularly in the central portion 442b of the second sheet 442 in the second region A2 is preferably configured to include silicone rubber. According to this configuration, silicone rubber which is friendly to the skin comes into contact with the wrist W. Accordingly, the inflatable portion 40 is less likely to adhere to the puncture site P. In addition, the silicone rubber having a relatively small coefficient of friction is located on the first surface (surface on the wrist W side). Accordingly, in a case where an external force is unintentionally applied to the hemostatic device 400 and the inflatable portion 440 is misaligned with the wrist W, it is possible to prevent the inflatable portion 440 from rubbing against the wrist W (particularly, the puncture site P). As a result, re-bleeding from the puncture site P can be suitably prevented.

In addition, in the inflatable portion 440, the marker 50 is disposed in substantially the center (substantially the center of the first sheet 41) on the second surface side located on the band 20 side. Since this marker 50 is disposed in the inflatable portion 440, the inflatable portion 440 can be rather easily aligned with the puncture site P. Accordingly, misalignment of the inflatable portion 440 is suppressed. The position of the marker 50 is not particularly limited, as long as the inflatable portion 440 can be aligned with the puncture site P. For example, in the inflatable portion 440, the marker 50 may be disposed in substantially the center (substantially the center of the second sheet 442) on the first surface side located on the wrist W side. In this case, in order to prevent the marker 50 from coming into direct contact with the puncture site P, it is preferable that the marker 50 is disposed on the inner surface side of the inflatable portion 440.

According to the hemostatic device 400 in Modification Example 4 described above, the second region A2 is disposed in both the first sheet 41 and the second sheet 442, and the second region A2 has a relatively large surface area. Accordingly, the gas contained inside the inflatable portion 40 can be more suitably discharged.

In addition, the second region A2 is also disposed in the central portion of the first surface (surface on the wrist W side). Therefore, the central portion of the second region A2 on the first surface side bulges most, and the peripheral edge portion of the second region A2 on the first surface side is separated from the wrist W. As a result, in addition to the space S1, a space S3 can be formed between the peripheral edge portion of the second region A2 on the first surface side and the band 20. Therefore, in the second region A2, an area of the portion exposed from the band 20 or the wrist W can be further increased, and the gas can be more satisfactorily discharged from the exposed portion.

Example

Figure 11A:
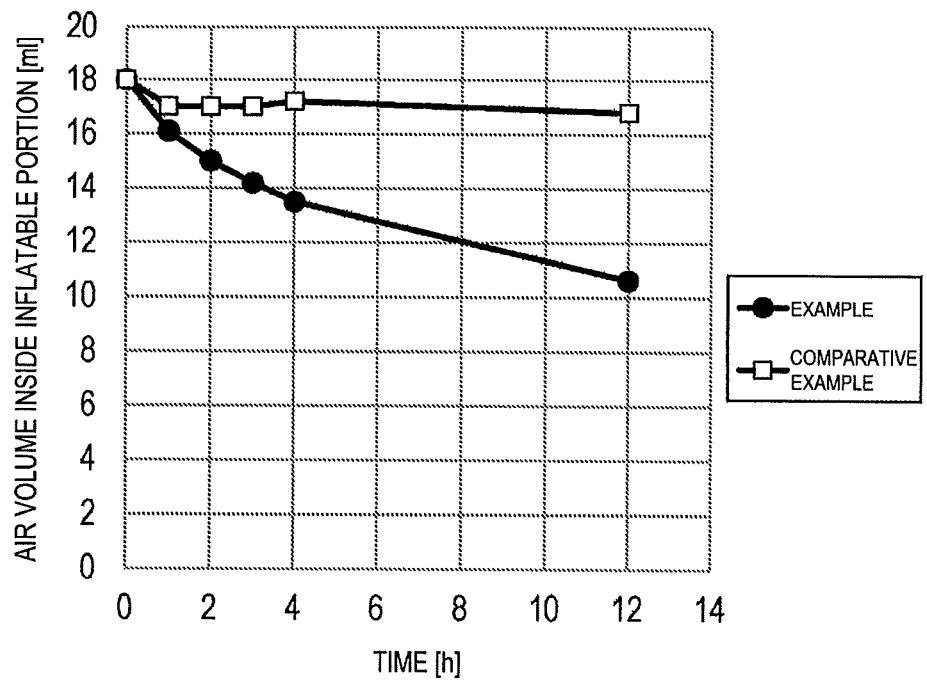
Figure 11B:
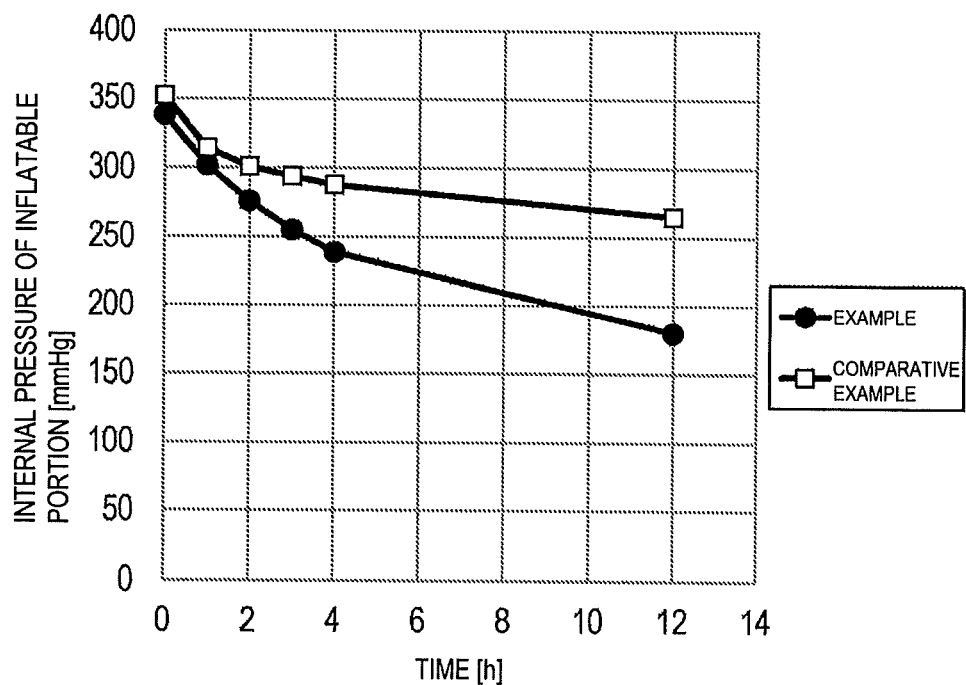
Figure 12:
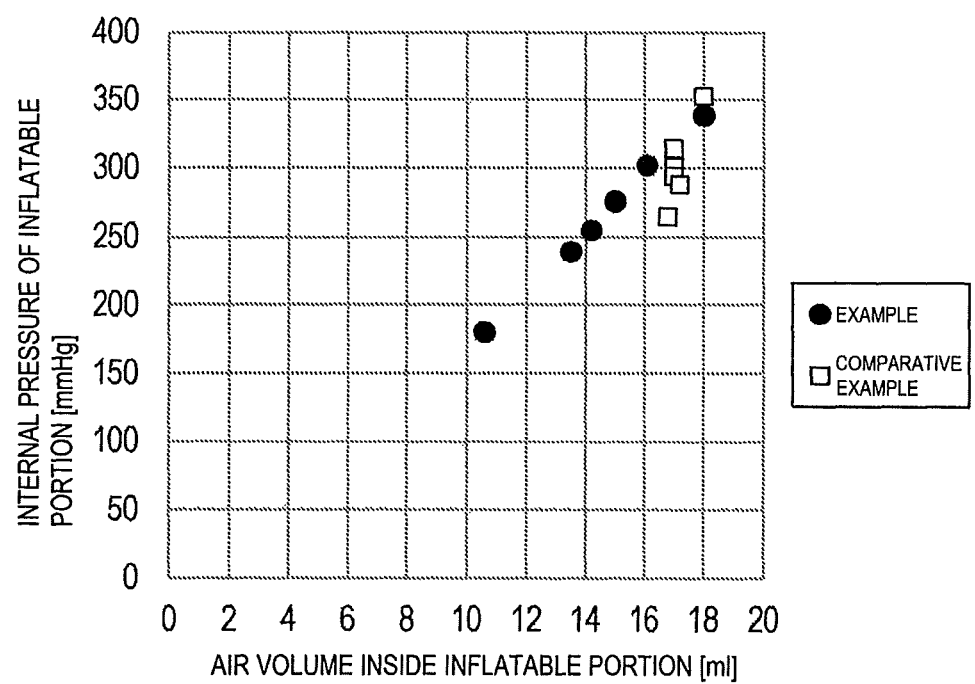
FIG. 12 is a view illustrating a relationship between the air volume inside the inflatable portion and the internal pressure of the inflatable portion according to the example and the comparative example.

FIGS. 11 and 12 are views for describing an example. Hereinafter, the example will be described with reference to FIGS. 11 and 12.

A first sheet and a second sheet were prepared as follows. In the first sheet, the peripheral edge portion was formed of polyvinyl chloride (the gas permeability coefficient is approximately $0.2 \times 10^{-8}$ cc·cm/cm²·sec·atm), and the central portion was formed of silicone rubber (the gas permeability coefficient is about $240 \times 10^{-8}$ cc·cm/cm²·sec·atm). The second sheet was formed of polyvinyl chloride. The peripheral edge portion of the first sheet and the peripheral edge portion of the second sheet were welded to each other to form an inflatable portion as illustrated in FIG. 7. The outer shape of each of the first sheet and the second sheet was a square shape whose one side length is 4.2 cm. The film thickness of the peripheral edge portion of the first sheet was 0.3 mm, the film thickness of the central portion of the first sheet was 0.5 mm, and the film thickness of the second sheet was 0.3 mm. In addition, in the first sheet, the surface area of the region formed of vinyl chloride was 1.64 cm². In the first sheet, the surface area of the region formed of silicone rubber was 16 cm².

In addition, the belt was produced using polyvinyl chloride. The length along the longitudinal direction of the belt was 290 mm, the width was 40 mm, and the film thickness was 0.5 mm. Then, one side of the peripheral edge portion of the inflatable portion was welded to the belt. In addition, a polycarbonate resin-made support plate in which both end portions were curved was inserted into a curved plate holder of the belt. As described above, a hemostatic device according to the example illustrated in FIG. 7 was produced.

Comparative Example

An inflatable portion was prepared by preparing a first sheet and a second sheet which were formed of polyvinyl chloride and welding the peripheral edge portion of the first sheet and the peripheral edge portion of the second sheet to each other. The outer shape of each of the first sheet and the second sheet was a square shape whose one side length was 4.2 cm and the film thickness was 0.3 mm.

In addition, the belt was produced using polyvinyl chloride. Note that, the length along the longitudinal direction of the belt was 290 mm, the width was 40 mm, and the film thickness was 0.5 mm. Then, one side of the peripheral edge portion of the inflatable portion was welded to the belt. In addition, a polycarbonate resin-made support plate in which both end portions were curved was inserted into a curved plate holder of the belt. As described above, a hemostatic device according to the comparative example was produced.

Test Method

The hemostatic devices according to the example and the comparative example were wrapped around a glass bottle having a diameter of 5.5 cm, and air of 18 cc was injected into each inflatable portion by using a dedicated syringe. Then, an air volume contained inside the inflatable portion was measured after 1 hour, 2 hours, 3 hours, 4 hours, and 12 hours from when the air was injected into the inflatable portion. Then, a change rate was calculated with respect to how the air volume contained inside the inflatable portion at each time changed from the air volume contained inside the inflatable portion measured immediately before. In addition, internal pressure of the inflatable portion was measured after 1 hour, 2 hours, 3 hours, 4 hours, and 12 hours from when the air was injected into the inflatable portion. Then, a change rate was calculated with respect to how the internal pressure of the inflatable portion at each time changed from the internal pressure of the inflatable portion measured immediately before. The results are shown in Table 1 below and FIGS. 11 and 12.

Test Results

TABLE 1

| | Example | | | | Comparative Example | | | |
|---|---|---|---|---|---|---|---|---|
| | Air Volume [ml] | Change Rate [%] | Pressure [mmHg] | Change Rate [%] | Air Volume [ml] | Change Rate [%] | Pressure [mmHg] | Change Rate [%] |
| When Air Is Injected | 18.0 | 100 | 338 | 100 | 18.0 | 100 | 352 | 100 |
| After 1 Hour | 16.1 | 89.4 | 302 | 89.3 | 17.0 | 94.4 | 314 | 89.2 |

TABLE 1-continued

|  | Example | | | | Comparative Example | | | |
| --- | --- | --- | --- | --- | --- | --- | --- | --- |
|  | Air Volume [ml] | Change Rate [%] | Pressure [mmHg] | Change Rate [%] | Air Volume [ml] | Change Rate [%] | Pressure [mmHg] | Change Rate [%] |
| After 2 Hours | 15.0 | 93.2 | 276 | 91.4 | 17.0 | 100 | 301 | 95.9 |
| After 3 Hours | 14.2 | 94.7 | 255 | 92.4 | 17.0 | 100 | 294 | 97.7 |
| After 4 Hours | 13.5 | 95.1 | 239 | 93.7 | 17.2 | 101 | 288 | 98.0 |
| After 12 Hours | 10.6 | 78.5 | 180 | 75.3 | 16.8 | 97.7 | 265 | 92.0 |

In the hemostatic device according to the example, as illustrated in Table 1 above and FIG. 11(A), the air volume contained inside the inflatable portion decreases with the passage of time, and thus, it is suggested that the air is discharged. Specifically, after 4 hours, an air volume of 4.5 ml was able to be discharged, from the air volume at the time when the air was injected into the inflatable portion. That is, after 4 hours, 25% of the initial air volume in the inflatable portion was able to be discharged.

In addition, in the hemostatic device according to the example, as shown in Table 1 above and FIG. 11(B), the internal pressure of the inflatable portion also decreases with the passage of time. Specifically, after 4 hours, the internal pressure at the time when the air was injected into the inflatable portion was able to be reduced by 99 mmHg. That is, after 4 hours, the internal pressure of the inflatable portion was able to be reduced to 70% of the initial internal pressure.

In addition, it has been found that in the hemostatic device according to the example, as illustrated in FIG. 12, there is a correlation between the air volume contained inside the inflatable portion and the internal pressure of the inflatable portion. This result indicates that in the hemostatic device according to the example, the internal pressure of the inflatable portion decreased over time as the air contained inside the inflatable portion was discharged.

In contrast, in the hemostatic device according to the comparative example, as shown in Table 1 above and FIG. 11(A), the air volume contained inside the inflatable portion does not decrease that much even if a certain time elapses. Therefore, it is suggested that the air is hardly discharged. Specifically, after 4 hours, an air volume of only 0.8 ml was able to be discharged, from the air volume at the time when the air was injected into the inflatable portion. That is, after 4 hours, only 4.4% of the initial air volume contained inside the inflatable portion was able to be discharged.

On the other hand, in the hemostatic device according to the comparative example, as shown in Table 1 above and FIG. 11(B), the internal pressure of the inflatable portion decreases with the lapse of time. Specifically, after 4 hours, the internal pressure at the time when the air was injected into the inflatable portion was able to be reduced by 64 mmHg. That is, after 4 hours, the internal pressure of the inflatable portion was able to be reduced to 81.8% of the initial internal pressure.

In addition, in the hemostatic device according to the comparative example, as illustrated in FIG. 12, a correlation was not found between the air volume contained inside the inflatable portion and the internal pressure of the inflatable portion. This result indicates that in the hemostatic device according to the example, the internal pressure of the inflatable portion does not decrease with the passage of time as the air contained inside the inflatable portion is discharged. In particular, in the hemostatic device according to the comparative example, as illustrated in FIG. 11(B), a decrease rate of the internal pressure is high after 1 hour from when the air is injected. Thereafter, the internal pressure relatively gently decreases. In the hemostatic device according to the comparative example, it is suggested that the internal pressure gradually decreases since the inflatable portion stretches with the lapse of time.

Even in a case where the inflatable portion stretches over time in this way, the compressing force acting on the puncture site can be reduced with the passage of time. However, if the inflatable portion is inflated and deformed over time, the contact area between the inflatable portion and the wrist increases. Accordingly, the nerves around the puncture site P is likely to be compressed, the wearer is likely to feel numbness or pain, and the compressing force does not concentrate on the puncture site P. Therefore, it is considered that the hemostasis effect is reduced. In addition, as described in the embodiment, the hemostatic device according to the example more easily performs the treatment in a case where the inflatable portion is excessively inflated, and the treatment in a case where the air needs to be injected again after the inflatable portion is inflated.

Hitherto, the hemostatic device according to the present invention has been described with reference to the embodiment and the modification examples. However, without being limited to only the respectively described configurations, the present invention can be appropriately modified.

For example, each portion configuring the hemostatic device can be substituted with any desired configuration which can fulfill the same function. In addition, any desired element may be added to the device.

In addition, without being limited to the hemostatic device used by being worn on the wrist, the present invention is also applicable to a hemostatic device used by being worn on a leg.

In addition, according to the above-described embodiment, the inflatable portion is configured to include the two sheets. However, the configuration is not particularly limited, as long as the inflatable portion includes the first region formed of the thermoplastic material and the second region formed of the thermosetting elastomer and is inflatable by injecting the gas. For example, the inflatable portion may be configured to include a single sheet, and may be formed in a bag shape by folding the sheet and adhering or welding edge portions of the sheet. In addition, the inflatable portion may be configured to include a balloon-shaped member which does not include the edge portions.

In addition, the first region may be disposed in a portion interlocking with at least the band, in the inflatable portion.

In addition, the position for providing the second region is not particularly limited. For example, the second region may be disposed across both the first surface located on the limb side and the second surface located on the band side, and may be disposed on only the first surface.

In the hemostatic device disclosed by way of example, the band and the inflatable portion interlock with each other by e welding. However, a configuration is not denied in which other members (for example, the first sheet and the second sheet, or the inflatable portion and the injection part) are adhered to each other using an adhesive.

The detailed description above describes embodiments of a hemostatic device and operational method representing examples of the inventive hemostatic device and operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
   a band for being wrapped around a site where bleeding is to be stopped on a limb;
   means for securing the band in a state where the band is wrapped around the limb;
   an inflatable portion that interlocks with the band, that is inflated by injecting gas, and that applies a compressive force at the site where bleeding is to be stopped;
   the inflatable portion including a first region formed of a thermoplastic material and a second region formed of a thermosetting elastomer whose gas permeability is higher than that of the thermoplastic material;
   the band including an interlock region which is formed of the thermoplastic material, and with which the inflatable portion interlocks; and
   the first region of the inflatable portion is welded to the interlock region of the band.

2. The hemostatic device according to claim 1, wherein the inflatable portion is located on a side of the band which faces the limb when the band is wrapped around the limb and is secured by the means for securing.

3. The hemostatic device according to claim 1, wherein the band is formed of a material whose elastic modulus is higher than a material of which the second region is formed.

4. The hemostatic device according to claim 1, wherein the inflatable portion has a first surface to be located on a side of the limb and a second surface to be located on a side of the band in a state where the band is wrapped around the limb, at least a portion of the second region being disposed in a central portion of the second surface.

5. The hemostatic device according to claim 1, further comprising: a sealing member that contains a material whose gas permeability is lower than that of the second region, and that detachably covers at least a portion of an outer surface of the second region.

6. The hemostatic device according to claim 1, wherein the second region is formed of the thermosetting elastomer whose gas permeability coefficient is 75 to 550 [×10-8 cc·cm/(cm$^2$·sec·atm)].

7. The hemostatic device according to claim 1, wherein the thermosetting elastomer is silicone rubber.

8. A hemostatic device comprising:
   a belt configured to be wrapped around a limb of a patient adjacent a site where bleeding is to be stopped;
   a plate more rigid than the belt, the plate being held by the belt;
   means for securing the belt in a wrapped state around the patient's limb;
   an inflatable portion that inflates upon injecting gas into an interior of the inflatable portion to apply a compressive force to the site at which bleeding is to be stopped;
   the inflatable portion including a first region and a second region, the first region being positioned along an outermost periphery of the inflatable portion and comprising a first plastic material, the second region being positioned inwardly of the first region and expanding outwardly when the gas is introduced into the inflatable portion to inflate the inflatable portion, the second region being comprised of a second plastic material different form the first plastic material;
   the second region possessing gas permeability allowing the gas introduced into the inflatable portion to inflate the inflatable portion to permeate through the second region over time to reduce pressure in the interior of the inflatable portion; and
   a portion of the first region of the inflatable portion being welded to a part of the belt to fix the inflatable portion relative to the belt.

9. The hemostatic device according to claim 8, wherein the belt is formed of a material whose elastic modulus is higher than a material of which the second region is formed.

10. The hemostatic device according to claim 8, wherein the inflatable portion comprises a first surface that faces the limb of the patient when the belt is in the wrapped state and a second surface that faces toward the belt when the belt is in the wrapped state, at least a portion of the second region being in a central portion of the second surface.

11. The hemostatic device according to claim 8, wherein the inflatable portion is comprised of a first sheet and a second sheet that are welded to one another, the first region of the inflatable portion being a region at which the first sheet and the second sheet are welded to one another.

12. The hemostatic device according to claim 8, wherein the gas permeability of the second plastic material from which the second region is fabricated is greater than the gas permeability of the first plastic material from which the second region is fabricated.

13. The hemostatic device according to claim 8, further comprising a sealing member fabricated from a material whose gas permeability is less than the gas permeability of the second plastic material from which the second region is fabricated, the sealing member being detachably applied to a portion of an outer surface of the second region of the inflatable portion.

14. The hemostatic device according to claim 8, wherein the second plastic material from which the second region is formed possesses a gas permeability coefficient of 75 to 550 [×10$^{-8}$ cc·cm/(cm$^2$·sec·atm)].

15. The hemostatic device according to claim 8, wherein the second plastic material is silicone rubber.

16. A hemostatic device comprising:
   a belt configured to be wrapped around a limb of a patient adjacent a site where bleeding is to be stopped;
   a plate more rigid than the belt, the plate being held by the belt;
   means for securing the belt in a wrapped state around the patient's limb;
   an inflatable portion that is inflated upon injecting gas into the inflatable portion to apply a compressive force to the site at which bleeding is to be stopped, the inflatable portion being fixed to the belt on a side of the belt that faces the limb of the patient when the belt is in the wrapped state;

the inflatable portion comprising a first surface that faces the limb of the patient when the belt is in the wrapped state and a second surface that faces toward the belt when the belt is in the wrapped state, the first surface or the second surface being comprised of a first region and a second region;

the first region being positioned outwardly of the second region and being made of a first plastic material, the second region being made of a second plastic material different from the first plastic material; and the first and second regions each possessing a respective gas permeability, the gas permeability of the second region being greater than the gas permeability of the first region to permit the gas introduced into the inflatable portion to inflate the inflatable portion to permeate through the second region over time to reduce pressure in the inflatable portion.

17. The hemostatic device according to claim 16, wherein the belt is formed of a material whose elastic modulus is higher than a material of which the second region is formed.

18. The hemostatic device according to claim 16, wherein the inflatable portion is comprised of a first sheet and a second sheet that are welded to one another, the first region and the second region being regions of the first sheet.

19. The hemostatic device according to claim 16, further comprising a sealing member fabricated from a material whose gas permeability is less than the gas permeability of the second region, the sealing member being detachably applied to a portion of an outer surface of the second region of the inflatable portion.

20. The hemostatic device according to claim 16, wherein the inflatable portion is comprised of a first sheet and a second sheet that are welded to one another at a weld area, the weld area being the first region.

* * * * *